United States Patent [19]

Ciemochowski

[11] 4,035,644
[45] July 12, 1977

[54] ATMOSPHERIC CONDITION DETECTING AND INDICATING APPARATUS AND METHOD

[76] Inventor: Michael F. Ciemochowski, 35523 Dunston Drive, Sterling Heights, Mich. 48077

[21] Appl. No.: 592,335

[22] Filed: July 1, 1975

[51] Int. Cl.$^2$ .................................... G01J 1/00
[52] U.S. Cl. .................... 250/340; 73/17 A; 250/338; 250/353
[58] Field of Search .......... 73/17 A; 250/338, 339, 250/340, 341, 349, 350, 351, 353

[56] References Cited

U.S. PATENT DOCUMENTS

| | | | |
|---|---|---|---|
| 3,077,763 | 2/1963 | Gena et al. | 73/17 A |
| 3,623,356 | 11/1971 | Bisberg | 73/17 A |

*Primary Examiner*—Davis L. Willis
*Attorney, Agent, or Firm*—Lon H. Romanski

[57] ABSTRACT

A photo-optic hygrometer comprising a thermocooler with a light reflecting surface has an infrared light beam directed against such surface by an infrared light emitting diode as to reflect such light beam against a phototransistor and place such phototransistor in conduction while, at the same time the reflecting surface is cooled by the thermocooler so as to thereby eventually cause dew formation on such surface; upon such dew formation the infrared energy is substantially absorbed by the dew thereby preventing the phototransistor from being conductive which, in turn, causes the reflecting surface to become somewhat heated thereby evaporating the dew and causing the above cycle to repeat. The monitored temperature of such reflecting surface at generally the cycle repeating temperature constitutes the dew point temperature which, along with other measured temperatures, such as ambient and/or structural surface temperatures are employed as inputs which through associated logic circuitry determine the energization and/or de-energization of related output means responsive to selected determined atmospheric conditions. The apparatus and method is employable in any desired atmosphere whether such be ambient or a closed atmosphere of a selected gas or mixture thereof.

22 Claims, 15 Drawing Figures

ATMOSPHERIC CONDITION DETECTING AND INDICATING APPARATUS AND METHOD

BACKGROUND OF THE INVENTION

Heretofore the prior art has proposed various systems, devices and apparatus for atmospheric condition detection, often referred to as "ice detection apparatus."

Among the various schemes heretofore proposed has been the development of systems which, in order to determine whether condensation formation is a possibility, attempt to determine relative humidity and the difference between ambient and a particular surface temperature. Various other prior art systems have also proposed the use of such humidistat type devices. Still other prior art devices rely on either chemical deposits or semiconductor material for moisture absorption. All of such prior art systems are not only costly but are very limited in accuracy and ambient temperature operating range and are thusly unsuitable to meet, for example, the present day requirements associated with the energy transmission and generating industry.

It is now proposed that extremely accurate and reliable atmosphere condition detecting systems can be constructed by employing a dew point determining stage which is based on energy absorption.

That is, light energy, as other forms of radiation, is emitted in small quantities called "quanta" and transmitted by electromagnetic waves. The production of light is attributed physically to actions taking place within atoms of the emitting source. Whitelight is in reality composed of many colors blended together. Such a whitelight beam, when refracted through a medium, such as a glass prism, disperses into a brilliant array, merging insensibly into one another and forming a spectrum.

Defining the spectrum requires specifying the vibration rate of the light source, or its corresponding wavelength. The relationship between these quantities is expressed by the equation:

$$C = f \cdot w$$

where:
$C$ = velocity of light
$f$ = frequency (vibration rate)
$w$ = wavelength In the prior art, the best known application of the detailed study of emission and absorption spectra is in the use in identifying elemental particles within a sample of an unknown composition as by recognition of the characteristic spectra.

Generally, the electromagnetic spectrum is classified by wavelength as, for example:
ultraviolet . . . 400nM–130nM
visible light . . . 400nM–760nM
infrared . . . 760nM–50,000nM Molecules may be considered as elastic arrays of electrically charged particles (atoms). Such particles, when subjected to electromagnetic radiation in the infrared region, will rotate or vibrate. Further, each specific molecule has a number of distinct frequencies of rotation and vibration.

When a molecule is subjected to infrared radiation of a frequency identical with one of its specific frequencies, it will be forced into vibration or rotation by absorption of energy from the infrared beam. Energy absorption measurements are recorded in terms of transmittance as a function of wavelength, with transmittance being defined as the energy (at a specific wavelength) emerging from a particular sample and expressed as a percentage of the energy entering that sample (also at the same wavelength). Accordingly, the percent transmittance as a function of wavelength is termed the infrared spectogram of the molecule, or, more commonly, its spectrum. Since the spectrum of each compound is unique, the infrared spectrum is often referred to as the "fingerprint" of a particular given compound.

Points of low transmittance in the spectra are termed absorption bands and the position of these bands (in the spectrum, depending on wavelength) identifies the compound while the depth of the absorption band can be related to concentration. Further, wavelength and frequency of infrared radiation are interrelated by the same formula:

$$C = f \cdot w$$

where:
$f$ = frequency
$w$ = wavelength
$c$ = velocity of light

Since velocity is constant $3 \times 10^{10}$ cm/sec (speed of light) each frequency of energy absorption can be identified by the wavelength of radiation. Wavelength expressed in microns (1 micron = $10^{-6}$ meters) has come to be the commonly accepted designation of regions of infrared spectrum, where specific molecules absorb energy.

The ability of a material to transmit infrared radiation is probably its most important characteristic.

Optical materials are used as windows or filters to admit infrared radiation, and as dispersing agents in the form of prisms to spread-out the radiation wavelength. Therefore, as employed by the invention, through the use of appropriate filters the desired infrared radiation can be obtained of any particular spectral span. This span, together with the selected spectral emission can be selected where water vapor absorption takes place.

Water vapor absorbs in the following broad spectral regions:
 a. infrared and microwave regions (where absorption is due to water vapor molecule rotation alone);
 b. infrared and occassionally the visible regions (where absorption is due to water vapor molecule vibration and rotation); and
 c. visible and ultraviolet regions (where absorption is due to water vapor molecule electron changes together with vibration and rotation).

As set-forth above, a relatively large total spectral region yields a possible basis for moisture sensors; however, the characteristics of each spectral band have attendant limitations due to the equipment required. For example, in the untraviolet region where a strong water vapor absorption band exists at 200 nM, the emission of this wavelength requires high voltage supplies and expensive vacuum tube sources. The vacuum tube source also has a very short life since its operation depends on a particular gas emitted in the ultraviolet spectral region by virtue of extremely high voltage excitation.

Accordingly, the invention herein disclosed employs the infrared regions (because many absorption bands are present) and in application to the invention's sensor detector operation, the associated equipment is solid state requiring typically low level voltage supplies. As will become apparent, the invention can be practiced by employing the above characteristics and using, in combination, an infrared light emitting diode and a phototransistor to thereby create a very accurate sensor device.

SUMMARY OF THE INVENTION

Method

According to the invention, generally, a method of determining the dew point temperature of a vaporized liquid carried within a gas atmosphere comprises the steps placing the gas atmosphere in intimate contact with a gauging surface, cooling the gauging surface until the vaporized liquid starts to percipitate from suspension as a dew onto said gauging surface, using the dew to absorb a sufficient degree of light energy to thereby prevent such light energy to energize associated photoresponsive means and to thereby cause heating of said gauging surface to thereby evaporate said dew, and monitoring the temperature of said gauging surface to determine the temperature at which such light energy was sufficiently absorbed in order to thereby determine the said dew point temperature.

APPARATUS

According to the invention, generally, the above method may be practiced by apparatus comprising gauging surface means comprises adapted to be situated within said gas atmosphere, means for cooling said surface means sufficiently to cause said vaporized liquid within said gas atmosphere to come out of suspension and precipitate as a dew upon said cooled gauging surface means, means for continually sensing the temperature of said surface means and effective for continually producing a temperature output signal in response thereto, and indicating means responsive to the formation of said dew upon said cooled gauging surface means, said indicating means being effective upon sensing the said formation of said dew to terminate further cooling of said surface means and generally substantially stabilize the magnitude of the then existing temperature of said surface means thereby resulting in said stabilized magnitude of temperature being said dew point temperature.

Various general and specific objects of the invention will become apparent when reference is made to the following detailed description considered in conjunction with the accompanying drawings.

BRIEF DESCRIPTION OF THE DRAWINGS

In the drawings, where for purposes of clarity certain details and/or elements may be omitted:

FIG. 15 is a simplified diagrammatic like view illustrating a further modification of the invention.

DETAILED DESCRIPTION OF THE PREFERRED EMBODIMENTS

Figure 1:
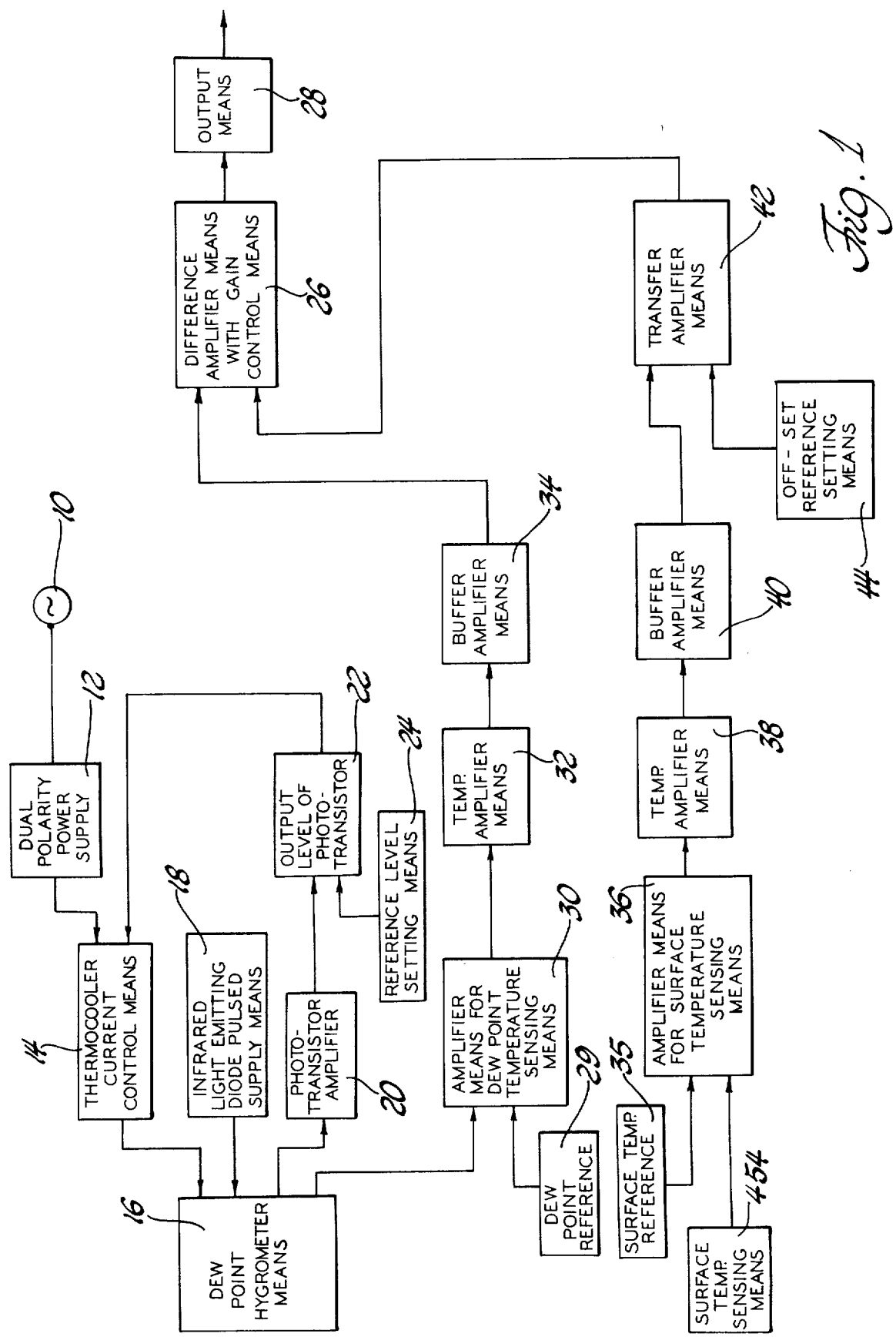
FIG. 1 is a diagrammatic illustration of the overall logic and circuitry employed in one particular embodiment of the invention.

Referring now in greater detail to the drawings, FIG. 1 illustrates in block diagram form one embodiment of an overall system employing the teachings of the invention. A source of electrical potential 10 is operatively connected to a dual polarity power supply means 12 which, in turn, is electrically connected to thermocooler current control 14 leading to associated dew point hygrometer means 16. A pulsed power supply means, for associated infrared light emitting diode means comprising the hygrometer 16, is shown at 18.

The signal means generated as by phototransistor means, comprising the hygrometer means, is applied to related phototransistor amplifier means 20 from where such amplified signal is directed to related means 22 which, depending on the value of the amplified signal and the particular value determined by the associated reference level setting or adjusting means 24, applied an output signal to the thermocooler current control 14. Generally, two channels, one concerned with the dew point temperature and the other with, for example, the surface temperature provide their ultimate signals to differance amplifier means 26 which, in turn, applies a related signal to associated output means 28. As generally depicted the dew point channel is illustrated as comprising amplifier means 30 for related dew point temperature sensing means, comprising a portion of the hygrometer 16, temperature amplifier means 32 and buffer amplifier means 34. The other channel is illustrated as comprising amplifier means 36 for associated surface temperature sensing means, amplifier 38, buffer amplifier means 40 and transfer amplifier means 42 with associated reference value setting means 44.

Figure 2:
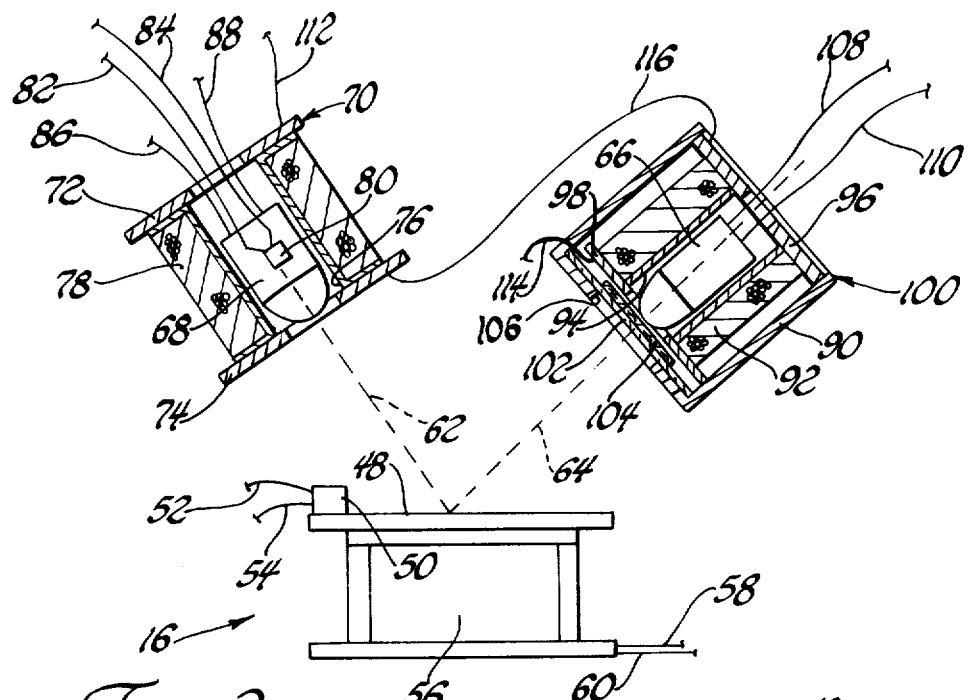
FIG. 2 is a simplified illustration of a sensor assembly, with portions thereof in cross-section, showing the general arrangement of the elements comprising such assembly.

FIG. 2, in which for purposes of clarity many of the details are not specifically shown because such omitted details and/or elements are well known in the art, illustrates the arrangement of the interrelated elements and sub-assemblies comprising, what may be referred to generally as, the hygrometer assembly 16.

Referring in greater detail to FIG. 2, a thermocooler assembly 56 (many of which are well known in the art) is shown as having an upper thermocooler surface 48 upon which is situated, in heat transfer relationship, temperature responsive electrical resistance means 50, having electrical leads fragmentarily illustrated at 52 and 54, with such resistance means 50 being effective to vary the voltage drop thereacross in response to and in relationship to the temperature of the thermocooler surface 48 as sensed by resistance means 50. The thermocooler 56 may, as is well known in the art, comprise a P-N junction type device whereby the passage of current in one direction causes a heating effect while the passage of current in the reverse direction causes a cooling effect. Accordingly, as shown in FIG. 2, fragmentarily illustrated electrical conductor means 58 and 60 are intended to depict such conductor means for the passage of current to the thermocooler 56.

As will become apparent, surface 48 is intended to serve as a reflecting mirror-like surface whereby a generally downwardly directed light beam, as depicted by 62, will strike the surface 48 and reflect along a path, as generally depicted at 64, so that such light beam will act upon, for example, a phototransistor 66.

The source of such light beam is an infrared light emitting diode (R-LED) 68 which, as generally shown, is situated and carried as within a spool like structure 70 having annular end portions 72 and 74 and an intermediate tubular portion 76. Situated about said tubular portion 76 and between end portions 72 and 74 is suitable heater means 78 which, may be of a single winding or, if desired, a plurality electrical resistance heaters annularly situated as to have their opposite ends generally parallel and respectively electrically connected to circuit means carried as by the end members or portions 72 and 74. Suitable temperature sensing means such as a thermocouple or a temperature responsive electrical resistance means 80 is provided in heat-transfer sensing relationship to R-LED 68 in order to at that point, in effect, monitor the actual temperature of the R-LED 68. The corresponding electrical conductor means leading to the R-LED 68 are fragmentarily illustrated at 82 and 84. Similarly, the electrical conductor means associated with the energization of R-LED 68 are fragmentarily illustrated at 86 and 88.

The phototransistor 66 is shown situated within and carried by a suitable holder assembly 90 which also contains resistance heater means 92 (which may be similar to 78) situated about the tubular portion 94 and between opposed annular end portions 96 and 98 of a spool like structure 100 similar to spool 70. The lower end of the holder 90 is open as at 106 across which is preferably provided a protective glass shield 102 and an infrared filter 104. The associated electrical conductor means leading to the phototransistor means 66 are fragmentarily illustrated at 108 and 110. If it is assumed that the resistance heater means 78 and 92 are in series with each other, than fragmentarily illustrated conductor means 112 and 114 would close the general circuit to associated power source means while conductor means 116 would interconnect the heater means 78 and 92.

Figure 3:
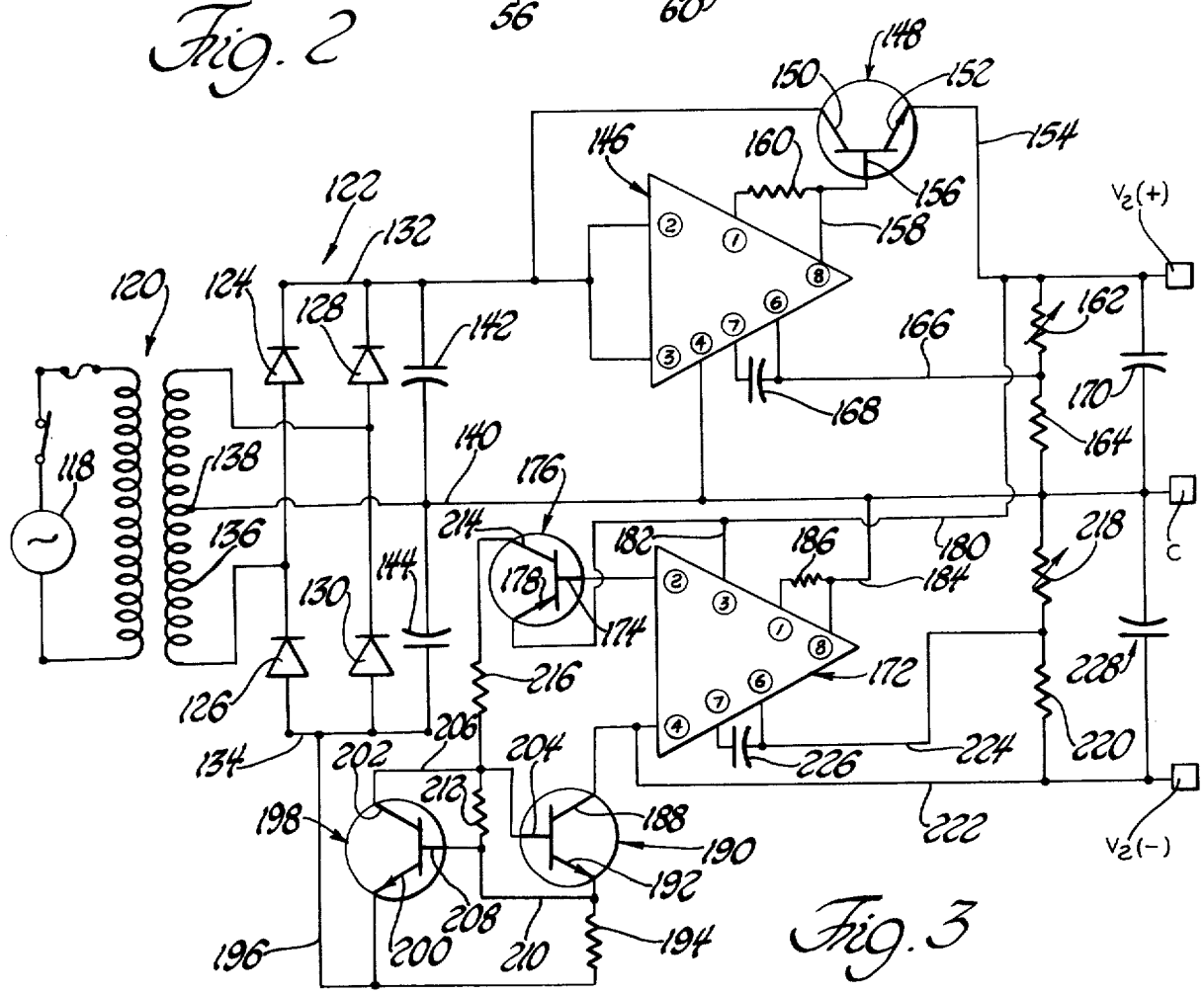
FIG. 3 is a schematic wiring diagram of a regulated main power supply employable in the invention.

FIG. 3 illustrates a schematic wiring diagram of the main power supply system for the logic circuitry employed by the invention as well as the power consumed by the R-LED 68. Referring in greater detail to FIG. 3, a suitable source of electrical potential 118, such as a 60 cycle 110 volt source, supplies power as through step-down transformer means 120 electrically connected to a full wave rectifier 122 having diodes 124, 126, 128 and 130 which are electrically connected to output conductors 132 and 134. The secondary winding 136 of transformer means 120 has a center or common tap 138 to which electrical conductor means 140 is connected. Capacitor means 142 and 144 are each connected to the common or ground conductor means 140 and respectively connected to conductors 132 and 134 to thereby filter the voltage ripple from the rectifier 122. An operational amplifier or regulator means 146 (having its terminal designations within circles) has its terminals 2 and 3 connected to the conductor means 132 and its terminal 4 connected to common conductor 140. An N-P-N transistor 148 has its collector 150 connected to conductor 132 while its emitter 152 is connected to conductor means 154 leading as to bus-like supply terminal or conductor means V(+). The base 156 of transistor 148 is connected to amplifier terminal 8 as by conductor 158 and, through resistance means 160 to amplifier terminal 1. The regulator means 146, generally, is limited as to its current carrying capacity and will not be capable of conducting relatively large currents. Accordingly, to be able to provide the necessary current flow, transistor 148 is turned "on" and "off" by regulator 146 and in so doing provides the required current flow through its collector-emitter circuit. A potentiometric voltage divider network across conductors 154 and 140 and comprised by a potentiometer 162 and resistance 164 is electrically connected via conductor means 166 to regulator terminal 6 and through capacitor means 168 to regulator terminal 7. By adjusting potentiometer 162, it becomes possible to thereby feed back a voltage signal to regulating means 146 indicative of the desired regulated value of voltage V(+) while the inputs at terminals 2 and 3 have the unregulated voltage applied thereto. The regulator 146, in response to such inputs causes the transistor 148 to be rapidly turned on and off in order to thereby maintain the desired magnitude of regulated positive voltage. In the preferred form, and as an extra precautionary measure, capacitor means 170 is provided across the common conductor 140 and regulated voltage conductor 154 in order to provide damping means and thereby positive assurance against the initiation and continuation of, for example, any self-induced oscillations as might occur within, for example, the regulator means 146.

A second amplifier-regulator 172 (which may in fact be identical to 146) has its terminal 2 connected to the base 174 of a P-N-P transistor 176 which has its emitter 178 connected via conductor means 180 to the V(+) regulated conductor 154. Terminal 3 of regulator 172 is also connected to 180 as by conductor 182 while the common conductor 140 is connected by conductor 184 and resistance means 186 to terminals 8 and 1, respectively of regulator 172. Terminal 4 of regulator 172 is connected to the collector 188 of an N-P-N transistor 190 which has its emitter 192 connected, through resistance means 194, to conductor means 196 leading to rectifier output conductor 134. A second N-P-N transistor 198 also has its emitter 200 connected to conductor 196 while its collector 202 is connected to the base 204 of transistor 190 as by conductor means 206. Base 208 of transistor 198 is connected via conductor means 210 to emitter 192 while resistance means 212 is placed across conductors 206 and 210. Further, collector 214 of transistor 176 is connected through resistance means 216 to conductor 206.

A second potentiometric voltage divider network, functionally equivalent to that across 154 and 140, comprised of a potentiometer 218 and resistance 220 is placed across the common conductor 140 and an output conductor 222 which leads from terminal 4 of regulator 172 to the bus-like output terminal or conductor means $V(-)$. A feedback conductor 224 leads from the voltage divider to terminal 6 and, through capacitor means 226, to terminal 7. A capacitor 228 functionally similar to capacitor 170 is placed across conductor means 140 and 222. The provision of transistors 190, 198 and 176 is, of course, to invert the signals with respect to the regulator 172 the output voltage of which is regulated as by the selective adjustment of potentiometer 218 in the same manner as regulation was achieved with potentiometer 162.

Figure 4:
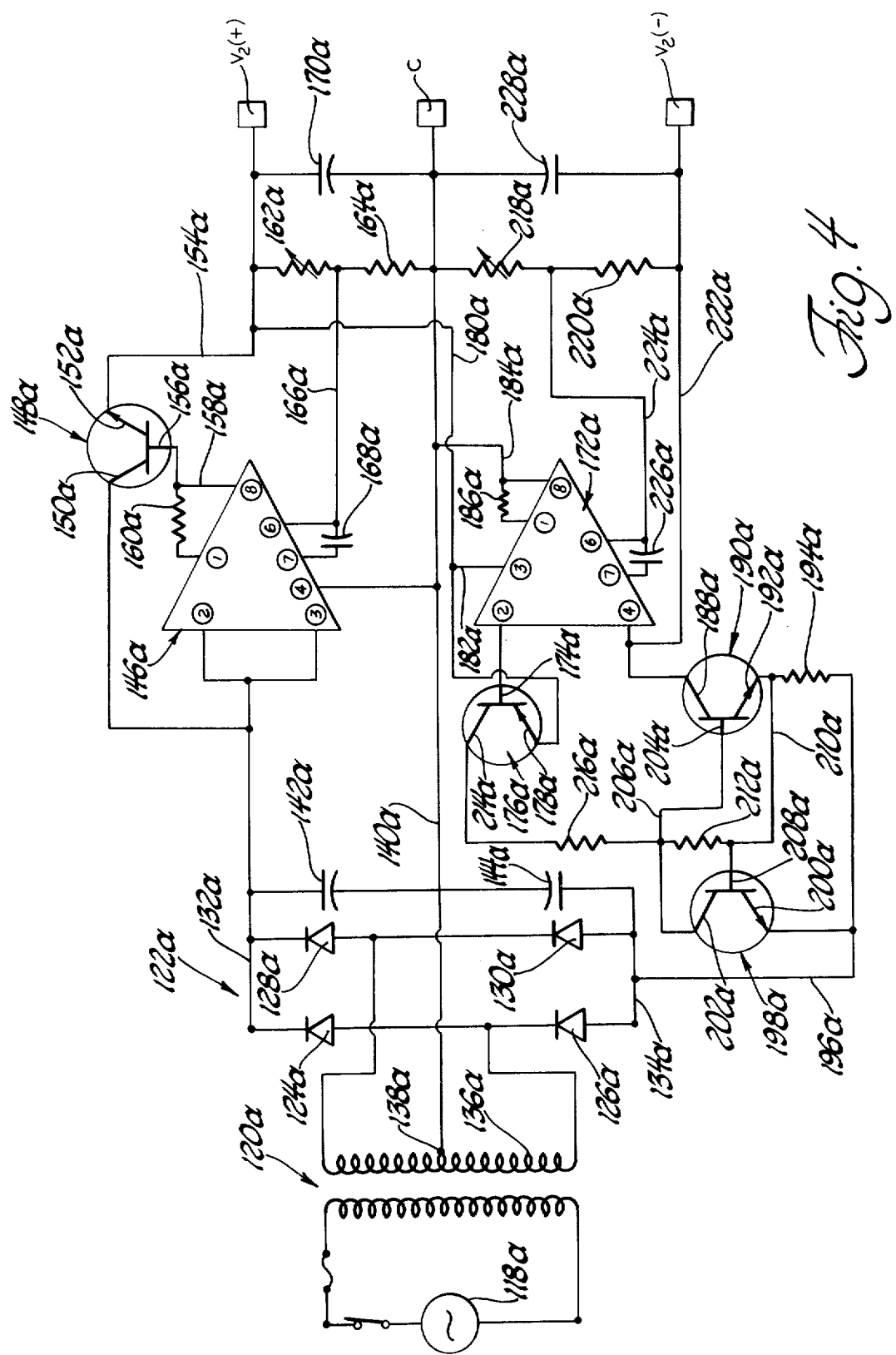
FIG. 4 is a schematic wiring deagram of a regulated power supply employable as the power source means for thermocooler means used in the invention.

FIG. 4 illustrates a second regulated power source for use in connection with the thermocooler 56. The circuitry and elements, generically, are as disclosed and described in FIG. 2 except for the fact that, in this particular situation, the magnitude of the regulated output voltage, both positive and negative, is less than that of FIG. 3. For ease of reference, the output bus-like terminals or conductors therefore, in FIG. 4 are value-identified by $V_2(+)$ and $V_2(-)$. All elements in FIG. 4 which are like or similar to those of FIG. 3 are identified with like reference numbers provided with a suffix a. The source of electrical potential, 118a, may, in fact be one and the same as 118 of FIG. 3.

Figure 5:
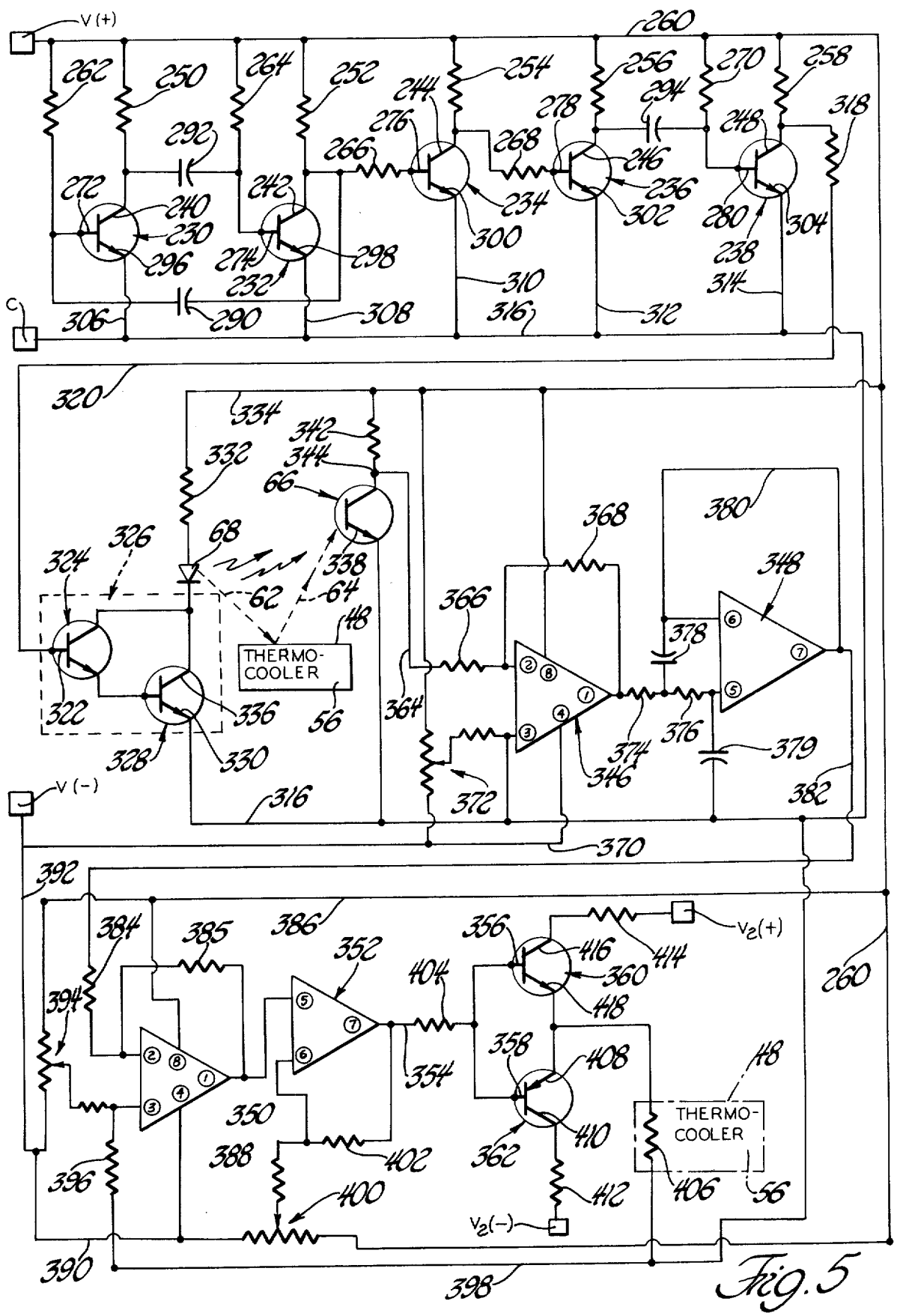
FIG. 5 is a schematic wiring diagram of one portion of one embodiment of the invention with such portion being used for the creation of a dew point temperature.

In FIG. 5, a first group of N-P-N transistors 230, 232, 234, 236 and 238 are illustrated as having their respective collectors 240, 242, 244, 246 and 248 electrically connected via respective resistances 250, 252, 254, 256, and 258 to suitable conductor means 260 leading as to the bus or conductor means $V(+)$. Additional resistors 262, 264, 266, 268 and 270 are provided in a manner as to place: (a) resistor 262 between base 272 of transistor 230 and conductor 260; (b) resistor 264 between base 274 of transistor 232 and conductor 260; (c) resistor 266 between base 276 of transistor 234 and collector 242 of transistor 232; (d) resistor 268 between 278 of transistor 236 and collector 244 of transistor 234; and (e) resistor 270 between base 280 of transistor 238 and conductor 260. A first capacitor 290 is connected as to have one electrical side thereof connected to base 272 and the other electrical side thereof connected to collector 242. A second capacitor 292 is situated as to have one electrical side thereof electrically connected to collector 240 and the other electrical side thereof connected to base 274, while a third capacitor 294 is situated as to have a first electrical side connected to collector 246 and the second electrical side thereof connected to base 280. The respective emitters 296, 298, 300, 302 and 304 are connected, as by respective conductors 306, 308, 310, 312 and 314 to suitable common or ground conductor means 316 leading as to the bus-like terminal means C. Transistors 230 and 232 comprise an astable multivibrator or oscillator with the frequency thereof being established, primarily, by the value of resistor 262. Generally, as transistor 230 is truned off, that is its non-conducting state, transistor 232 is turned on or, in other words, its conducting state, with the reverse also being true. Therefore, when transistor 232 is off transistor 234 is forwardly biased and is turned on thereby creating a negative $(-)$ pulse which is applied to the base 278 of transistor 236. The application of the negative pulse to the base 278 of transistor 236 serves to better assure, during that time, that transistor 236 does not turn on and go into conduction.

Capacitor 294 and resistor 270 comprise an R-C network serving to form a timing circuit for establishing the time duration during which transistor 238 is held off in order to thereby provide a positive pulse as at its collector 248 and applied through resistor means 318 and conductor means 320 to the base 322 of a transistor 324 of a Darlington circuit 326 having a second direct coupled complementary transistor 328. The emitter 330 of transistor 328 is connected to common conductor means 316. The R-LED 68, along the series resistance means 332, is connected as between conductor means 334, leading to $V(+)$ conductor means 260, and the collector 336 of transistor 328. Transistor 328 will turn on and off in accordance with the frequency established by the astable oscillator of transistors 230 and 232 and, when turned on will remain on for a duration determined by the pulse width established transistors 236 and 238 in conjunction with the timing circuit comprising capacitor 294 and resistor 270.

When transistor 328 turns on the R-LED 68 is energized to emit a high energy infrared light as by the application thereto of, for example, 10.0 amperes for a 100 microsecond duration. By maintaining a selected pulse width as described above it becomes possible to apply high currents to the R-LED 68 because the overall cycle or frequency is also selected as to provide sufficient recovery time for the R-LED 68 thereby preventing damage thereto while still being able to obtain energy output levels therefrom much higher than what could be tolerated as a constant condition.

Everytime that the pulsed infrared light beam strikes surface 48 and reflects against phototransistor 66, such transistor 66 is turned on thereby completing a circuit through the emitter 338 and collector 340 thereof and effectively, because of resistor 342, bringing point 344 to the potential of common (C) conductor 316.

FIG. 5 also illustrates an operational amplifier 346, an integrating amplifier 348, an inverting amplifier 350 and an output amplifier 352 the output of which is applied via conductor means 354 to respective bases 356 and 358 of N-P-N transistor 360 and P-N-P transistor 362. The collector 340 of phototransistor 66 is electrically connected via conductor means 364 and resistor means 366 to the inverting terminal 2 of amplifier 346. Further, the output as at terminal 1 is fed back through resistance means 368 to the same input terminal 2. Terminals 8 and 4 of amplifier 346 are respectively connected to the $V(+)$ of conductor means 334 and the $V(-)$ of conductor means 370. The inverting amplifier 346 is selectively off-set as by related potentiomenter means 372 connected to terminal 3 of amplifier 346.

Terminal 5 of integrating amplifier 348 is connected via resistors 374 and 376 to the output of inverting amplifier 346 as well as to terminal 6 of amplifier 348 by means of capacitor 378 and to the common conductor 316 as through capacitor 379. As indicated, there is unity amplification via conductor means 380 from the output terminal 7 to input terminal 6 of integrating amplifier 348.

Accordingly, the negative pulse inputs at terminal 2 of amplifier 346 are inverted as a positive pulse output and applied to terminal 5 of integrating amplifier 348 where such positive pulses are integrated to provide a d.c. output at terminal 7 of amplifier 348 to be applied, through conductor means 382 and resistor means 384, as an input to terminal 2 of inverting amplifier 350.

The output at terminal 1 of amplifier 350 is fed back via resistor 352 to input terminal 2 via resistor 385, while terminals 8 and 4 thereof are respectively connected to the V(+) value of conductor means 386 leading to conductor means 260, and the V(−) value of conductor means 370 as by conductor means 388, 390 and 392. Terminal 3 of amplifier is connected to an adjusting potentiometer 394 as well as to the common ground or conductor means 316 as by resistance means 396 and conductor means 398. The potentiometer 394 is adjusted to achieve the desired off-set.

Amplifier 352 is similarly provided with potentiometer means 400 in association with the feedback resistor 402 in circuit between the output terminal 7 and the input terminal 6 of amplifier 352 thereby enabling the selective adjustment of the degree of amplification from input terminal 5 to output terminal 7 of amplifier 352.

As a consequence of the inverting function of amplifier 350, the positive d.c. input at terminal 2 of amplifier 350 results in an amplified output of opposite polarity at terminal 1. The amplified negative signal is then applied as an input to terminal 5 of amplifier 352 which serves to buffer and somewhat amplify the signal and apply it, through resistance means 404, to bases 356 and 358 of transistors 360 and 362. Since the signal or valtage thusly applied to bases 356 and 358 is negative while transitors 360 and 362 are respectively N-P-N and P-N-P, only transistor 362 will be turned on thereby permitting current flow from conductor 398 through the P-N junction device 406, emitter 408 collector 410, resistor 412 and to the bus-like terminal or conductor means at a value of V$_2$(−) with such current flow through device 406 causing a cooling effect continually lowering the temperature of thermocooler surface 48.

Assuming now, for example, that surface 48 is presented as to the ambient air flow forward of, for example, the inlet of a turbine engine, as the surface 48 continues to cool the ambient air passing thereacross and/or impinging thereagainst will at some particular temperatur of surface 48 cause moisture carried by or forming an integral part of such ambient atmosphere to precipitate onto such cooled surface 48. By definition, the temperature at which such moisture is thusly precipitated or deposited constitutes the dew point of such ambient air.

As soon as such moisture becomes present on surface 48 of the thermocooler 56, the pulsed infrared energy produced by the R-LED 68 becomes sufficiently absorbed and whatever infrared energy which might remain to travel along path 64 is not sufficient to place phototransistor 66 into conduction. With transistor 66 thusly kept off the pulse produced as at point 344 is of a positive value and not of the negative value previously described. Accordingly, the amplified output at terminal 7 of amplifier 352 becomes a positive value voltage which when applied to transistors 360 and 362 causes transistor 362 to be held off while biasing transistor 360 into conduction thereby permitting a reverse direction of current flow namely from the bus-like terminal or conductor means at a value of V$_2$(+) through resistor means 414, collector 416, emitter 418, P-N junction device 406 and into conductor means 398 leading to conductor means 316 at the common ground.

The thusly caused reverse flow of current through P-N junction deivce 406 causes a heating effect on surface 48 of thermocooler 56 with such heating effect continuing and resulting in the effective evaporation of the previously precipitated moisture on surface 48. The removal of such moisture again permits the pulsed infrared energy of the R-LED 68 to cause phototransistor 66 to go into conduction with the resulting consequence that moisture is again deposited on thermocooler surface 48. The above system will quickly cycle back-and-forth at the thusly established dew point temperature (for the then existing conditions of ambient air) and such dew point temperature will be sensed by temperature responsive resistance means or RTD 50 (FIG. 2) which is continually responsive to the surface temperature of thermocooler surface 48. The resistor 50 may be preferably, of linear characteristics. It should be realized, of course, that the actual temperature sensed when moisture forms on surface 48 will be less than the temperature at which such moisture is finally eliminated by the heating of the surface 48. Accordingly, such temperatures do establish the temperature limits of at least a small region wherein the true dew point temperature does actually exist. However, since the cyclic operation is extremely rapid, the actual temperature region is very narrow.

Figure 6:
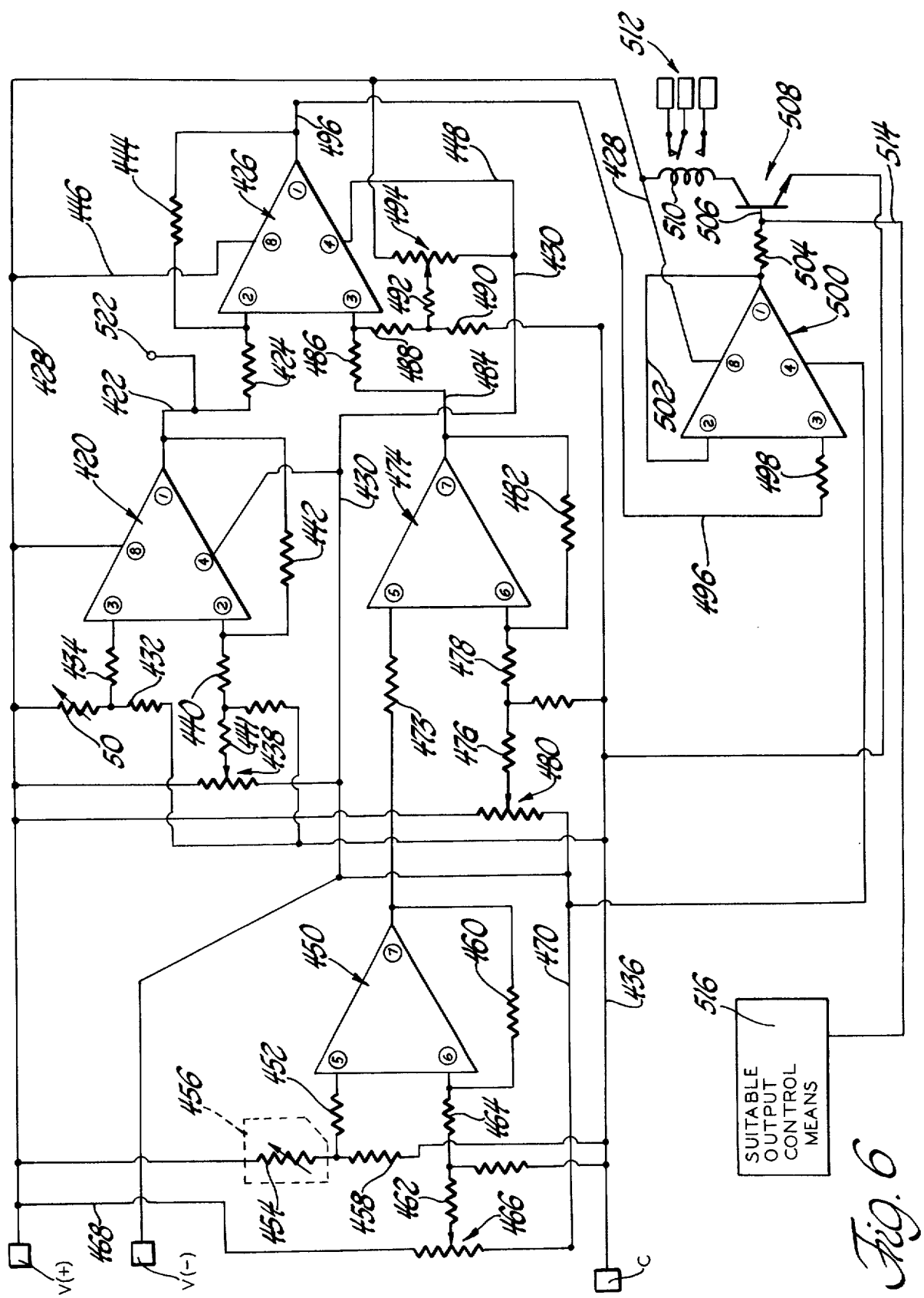
FIG. 6 is a schematic wiring diagram of circuitry employable as in combination with that of FIG. 5 for sensing additional parameters, such as a monitored surface temperature, and, in response to logic criteria, producing a suitable output.

Referring to FIG. 6, an operational amplifier 420 is shown as having its output terminal 1 connected via conductor means 422 and resistor 424 to the input terminal 2 of a comparator amplifier 426. Terminals 8 and 4 of operational amplifier 420 are respectively connected to conductor means 428 and 430 which, in turn, respectively lead to the bus-like power output terminals or conductor means at values V(+) and V(−). The variable temperature responsive resistance means 50 and resistance means 432 comprise a potentiometric type of input into terminal 2 of amplifier 420 as through resistor 434. As can be seen, the variable resistance means 50 is connected to conductor means 428 while resistance means 432, connect-d to variable resistor 50, is at its other end connected to conductor means 436 leading to the ground or common value, C.

A potentiometer 438, the resistor of which is connected across conductors 428 and 430, may be adjusted as to establish a reference voltage value which is applied, as through resistors 440 and 441, to the input terminal 2 of amplifier 420. The output at terminal 1 is also fed back via resistor 442 to the input of terminal 2. For purposes of discussion, let it be assumed that potentiometer 438 has been so adjusted as to result in an output of "0" at terminal 1 of amplifier 420 when the resistor 50 indicates a dew point temperature of 32° F. (It should be mentioned that the particular reference value can be any value selected to meet the requirements of the situation.) Under such conditions, the value of the d.c. output at terminal 1 of amplifier 420 is directly proportional to the temperature of the thermocooler. The output of amplifier 420 is applied to the negative input terminal 2 of a second operational amplifier 426 the output of which, as at its terminal 1, is fed back into the same negative input terminal 2 as through resistor 444. Terminals 8 and 4 are respectively connected, as through conductors 446 and 448, to V(+) conductor means 428 and V(−) conductor means 430.

Another operational amplifier 450 has its positive input terminal 5 connected through resistor means 452 to a potentiometric input device comprised of a second linearly variable temperature responsive resistance means 454 which is in temperature sensing relationship to the ambient atmosphere or, if desired, to the actual surface of the particular structure being monitored and to be protected. For example, for purposes of illustration, let it be assumed that the actual surface in question is the inlet surfce 456 of a turbine engine and that the variable resistance 454 is in heat transfer and sensing relationship thereto. The other end of resistor 454 is connected to the V(+) value of conductor means 428 while resistance means 458, connected to 454 and 452, is connected to conductor means 436 leading to the common terminal means, C.

The output at terminal 7 of amplifier 450 is fed back, via resistor 460, to the negative input teminal 6. Further, a second off-set signal, generated as by reisistors 462 and 464 along with potentiometer 466, the resistance element of which is connected across conductor means 428 and 430 as by conductors 468 and 470, is applied to the same negative input terminal 6. Again, for purposes of discussion, let it be assumed that the potentiometer 466 is so adjusted as to result in a 0 output at terminal 7 and on conductor 472 when the temperature sensed by variable resistance means indicates a value of 32° F. Of course, under such conditions, the value of the output votage on conductor 472 will be proportional to the surface (or ambient air) temperature sensed by resistor means 454.

The output voltage from amplifier 450 is applied, through resistor 473, to the positive non-inverting input terminal 5 of a follower amplifier 474. An off-set voltage, generated as by resistors 476 and 478 along with potentiometer 480, the resistance element of which is connected across conductor means 428 and 430, is applied to the negative input terminal 6. Further, the output at terminal 7 is fed back via resistance means 482 to the same negative input terminal 6. the potentiometer 480 is so selectively adjusted as to result in the output at terminal 7 being of a voltage value of 0 whenever the output of amplifier 450 and the corresponding input to terminal 5 of amplifier 474 is a positive voltage. Therefore, the output at terminal 7 of amplifier 474 will only be an amplified voltage value, in the negative direction, of only such inputs to terminal 5 of amplifier 474 as are negative in value. This, in turn, orients the entire system to the selected "freezing" temperature of 32° F. (It should be clear that the 32° F. temperature is merely illustrative and in actual practice, the actual reference temperature might be, for example, 34° F. so as thereby provide for some degree of anticipation and attendant lead time to take corrective action. In other words, the monitored structure may well be of the type which can not tolerate even the start of actual freezing conditions and therefore appropriate corrective or preventive action has to be initiated in anticipation to thereby prevent the occurrence of the actual freezing condition.)

The output at terminal 7 of amplifier 474 is applied via conductor means 484 and resistor means 486 to the positive input terminal 3 of comparator amplifier 426. A biasing network comprises resistors 488, 490 and 492 along with potentiometer 494, the resistive element of which is across conductor means 428 and 430, and is operatively connected to the input terminal 3 of amplifier 426. Generally, since amplifier 426 is a comparator, when the value of the signals applied to the input terminals 2 and 3 thereof by amplifiers 420 and 474 are equal, the output voltage of amplifier 426, at its terminal 426, will be 0. Potentiometer 494 provides the means for, generally, altering such result by being able to alter the actual value of the input signal to terminal 3 as to cause amplifier 426 to read a different value of input than that actually existing at the output of amplifier 474. For example, if this were done an output signal of 0 from amplifier 474 might actually be changed to an input signal of some negative value thereby creating a difference as between input terminals 2 and 3 and amplifying such difference and producing such as an output at terminal 1 of amplifier 426. This feature may well be suited for situations where it is previously determined that one cannot wait for the event when, for example, surface temperature equals dew point and that the monitored structure or surface must have corrective action initiated prior to surface temperature actually equalling dew point. In effect, potentiometer 494 can establish a fixed differential within amplifier 426 with regard to the magnitude of the actual output values produced by amplifiers 420 and 474. When equality of signals from the dew point sensor and the surfce temperature sensor is attained, the output from terminal 1 of amplifier 426 is applied via conductor means 496 and resistance means 498 to the positive input terminal 3 of buffer amplifier 500. Terminals 8 and 4 of such amplifier 500 are respectively connected to conductor means 428 and 430 respectively at values of V (+) and v(−), while the output at terminal 1 is fed back via conductor means 502 to the negative input terminal 2. The resulting output at terminal 1, which may be applied through resistance means 504 to base 506 of transistor 508 serves to place transistor 508 into conduction and thereby energize, for example, coil means 510 of suitable related relay means 512 or to provide any other signal as along conductor means 514 to any related or associated indicator, warning or control means 516.

Figure 7:
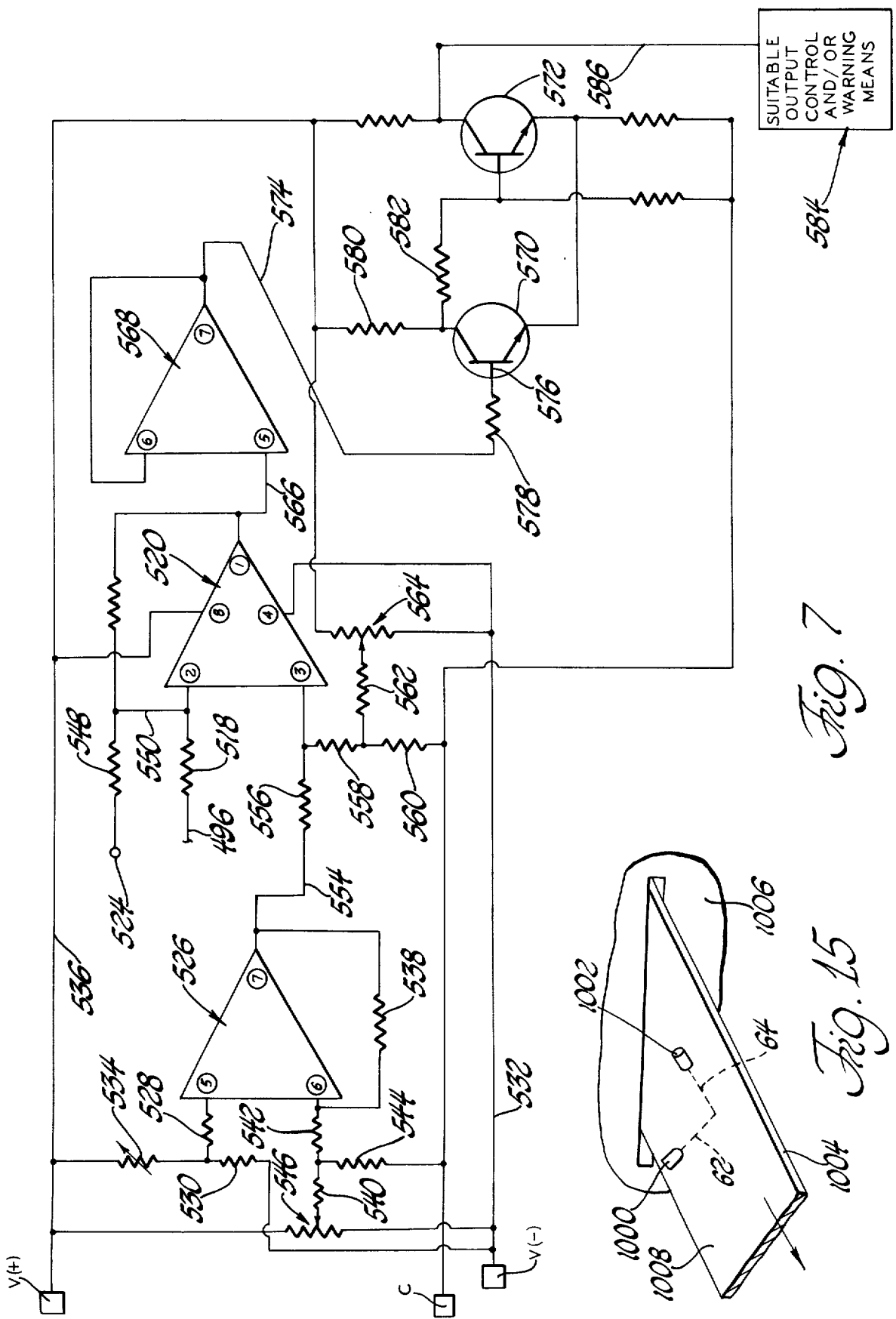
FIG. 7 is a schematic wiring diagram illustrating a modification of the invention and, generally, being effective to replace and function in the stead of the circuitry of FIG. 6.

FIG. 7 may be considered a modification of the invention as thus far disclosed through FIGS. 1 to 6. That is, the modification contemplates, for example, the removal of amplifier 500 and related circuitry along with such as transistor 508, relay 512, etc. and the substitution therein of the circuitry of FIG. 7. That is, in the modification output conductor 496 from amplifier 426 would be connected through resistor means 518 to the negative input terminal 2 of an amplifier 520 while a terminal 522 connected to conductor 422 of FIG. 6 would be connected to terminal 524 of FIG. 7.

An operational amplifier 526 has its positive input terminal 5 connected as through a resistor 528 to a point generally between a resistor 530, the other end of which is electrically connected to conductor means 532 which is at a voltage value V(−), and a linearly temperature responsive variable resistance means 534 which has its other end electrically connected as to conductor means 536 at a voltage value V(+). Temperature sensing and responsive resistance means 534 is positioned as to be acted upon and responsive to ambient air temperature. The output of terminal 7 of amplifier is fed back via resistor 538 to the negative input terminal 6. Further, biasing or off-set means, comprised of resistors 540, 542 and 544 along with a potentiometer 546, the resistive element of which is placed across conductor means 536 and 532, provide a selected voltage signal to input terminal 6 of amplifier 526.

When amplifier 426 of FIG. 6 turns on, the output therefrom is applied via conductor means 496 and resistor 518 to the input terminal 2 of amplifier 520 of FIG. 7. At the same time, the dew point signal on terminal 522 of FIG. 6 is also applied to terminal 524 and, through resistor means 548 and conductor means 550 to the same input terminal 2 of amplifier 520. The output at terminal 1 of amplifier 520 is fed back via resistance means 552 to the same input terminal 2. Further, terminals 8 and 4 are respectively electrically connected to conductor means 536 and 532. The output at terminal 7 of amplifier 526 is applied along conductor 554 and resistor 556 to the other input terminal 3 of amplifier 520. Additionally a biasing network or off-set means comprised of resistors 558, 560 and 562 along with a potentiometer 564, which has its resistive element across conductor means 536 and 532, provides a selected signal also applied to the same input terminal 3. When the signals are all present, that is on terminal 524, conductor 496 and conductor 554, amplifier 520, which functions as a summation amplifier, produces an output at its terminal 1 and applies it via conductor means 566 to the input terminal 6 of a buffer amplifier 568.

There will always be an input on terminal 524 but not always will there be an input on conductor 496. Since amplifier 520 is a summing amplifier there will be much less amplification when only an input exists on terminal 524 than when an input also exists on conductor 496 and conductor 554. Since such signals are always present from the ambient atmospheric temperature sensing means as well as the dew point sensing means, the only lacking signal is that from amplifier 426 which will occur at equality at some temperature below the reference point.

Transistors 570 and 572 conprise a Schmidt Trigger circuit and are set to turn on at a predetermined threshold voltage. Therefore, the system is so set as to provide a sufficient amplified voltage on conductor 566 and a resulting sufficient amplified voltage on conductor means 574 leading to base 576 of transistor 570 to turn transistor 570 on only when there is the presence of a signal on conductor 496 from amplifier 426 of FIG. 6. The tripping of the Schmidt Trigger is determined by the values of resistors 578, 580 and 582. When transistor 572 is thusly turned on suitable associated output control and/or warning means or relay means 584 may be energized as through conductor means 586. In some instances such associated means may take the form of heating means for heating the particular monitored surface with which the overall system is concerned. Some such devices have taken the form of relay operated electrical heating means while others, especially where turbine engine inlet surfaces are concerned, have provided a controlled degree of engine exhaust recirculation into the intake to thereby, at that point, raise the temperature of the monitored surface and even possible increase the dew point temperature within the intake area. The provision of such a Schmidt Trigger results in an arrangement whereby there is an inherent threshold and hysteresis in the system so that once the output means 584 is actuated it remains so until a charge occurs in either or both the sensed ambient temperature or dew point temperature to thereby indicate operation within a safe region. This feature avoids excessive rapid cycling of the associated output means, such as heater means in a turbine engine, and provides for any desired extended stability of such associated output means 584.

Figure 8:
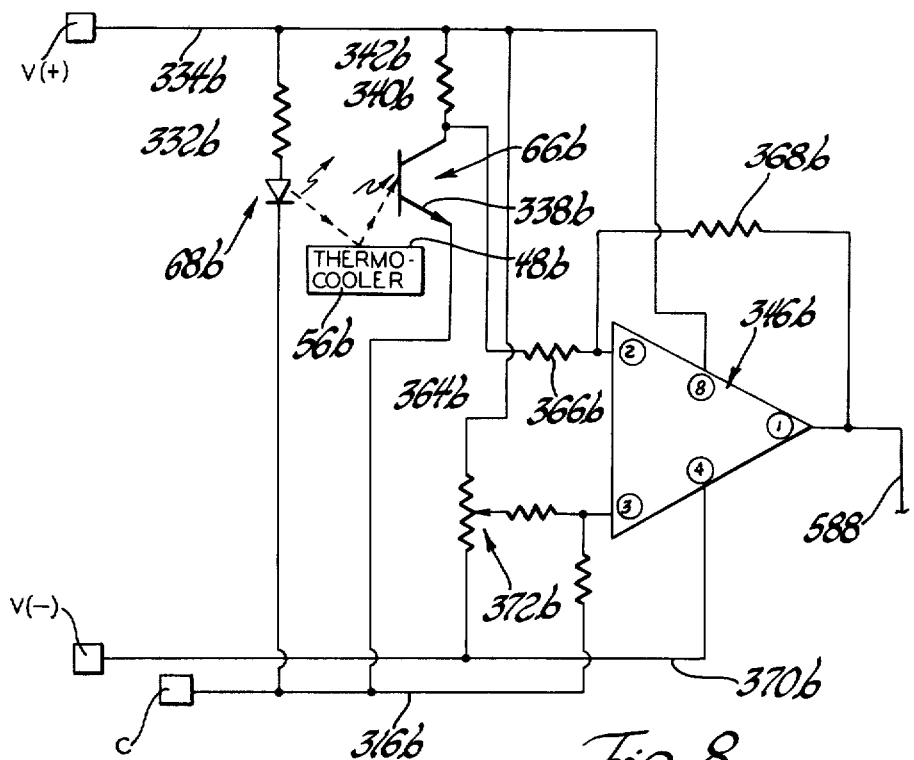
FIG. 8 is a fragmentary schematic wiring diagram illustrating, fragmentarily, a modification of the circuitry of FIG. 5.

FIG. 8, fragmentarily, illustrates another embodiment of the invention. All elements in FIG. 8 which are like or similar to those of FIG. 5 are identified with like reference numbers provided with a suffix *b*. The basic change contemplated by FIG. 8 would be the substitution thereof for the like elements in FIG. 5 and the elimination of the circuitry for establishing cycle times and pulse width durations as described with regard to FIG. 5. That is, the embodiment of FIG. 8 contemplates a constantly energized, by a relatively lower d.c. voltage, R-LED 68b as to continuously, and not pulsed, apply the infrared energy to surface 48b of the thermocooler. Further, since in such an embodiment there would not be the need for integrating the pulses, integrating amplifier 348 of FIG. 5 could be eliminated and the output of amplifier 346b would be applied to conductor means 588 leading directly to the input terminal 2 of amplifier 350 of FIG. 5. Except for the changes noted, the rest of the circuitry of FIG. 5 would remain intact and operate in the manner specifically described with reference thereto.

Figure 9:
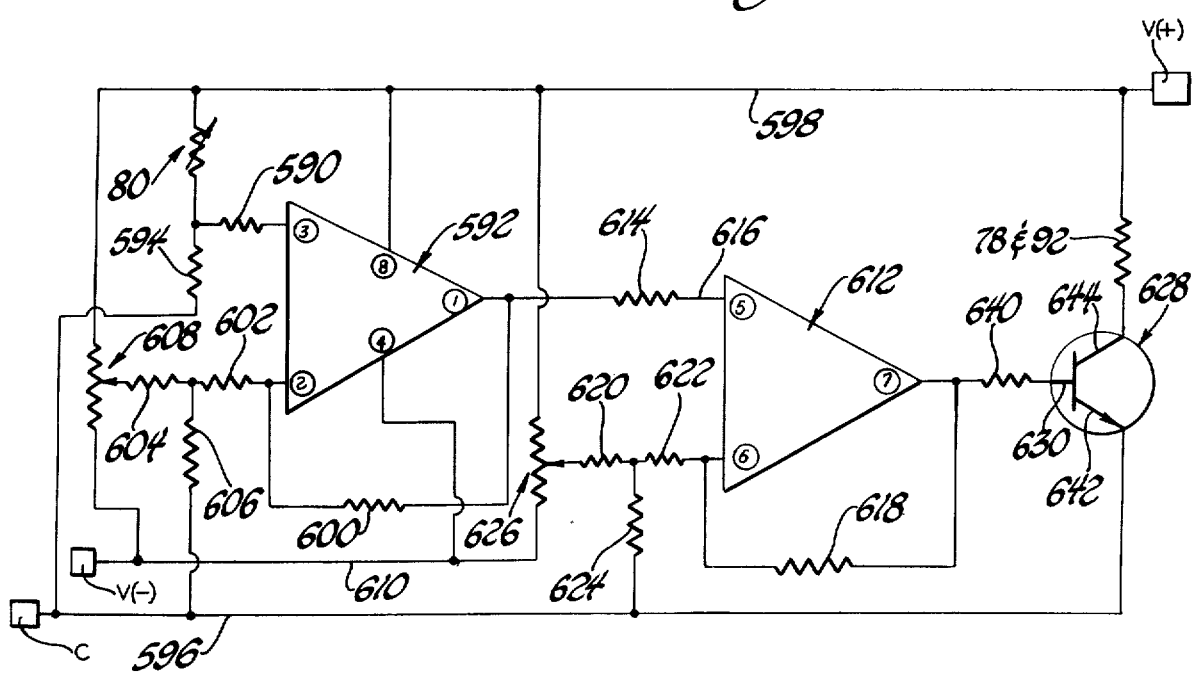
FIG. 9 is a schematic wiring diagram illustrating circuitry employable for maintaining at least a desired range of temperatures for at least the infrared light emitting diode of FIG. 2.

FIG. 9 illustrates the R-LED 66 heater control circuitry. The temperature sensing and linearly responsive resistor 80 is connected at one end to a resistor 590, leading to input terminal 3 of amplifier 592, and to a resistor 594 the other end of which is connected to conductor means 596 which is at common ground potential C. The other end of resistor 80 is connected to conductor means 598 leading to terminal or circuit means at a voltage value V(+). The output at terminal 1 of amplifier 592 is fed back via resistor means 500 to input terminal 2. Additionally, biasing or off-set means comprising resistors 602, 604 and 606 along with a potentiometer 608 the resistive element of which is connected across conductors 598 and 610, the latter being at a voltage value V(−).

A second amplifier 612 has its input terminal 5 electrically connected to output terminal 1 of amplifier 592 as by resistor means 614 and conductor means 616. The output at terminal 7 of amplifier 612 is fed back via resistor 618 to its input terminal 6. Further, a biasing or off-set network comprised of resistors 620, 622 and 624 along with a potentiometer 626, the resistive element of which is connected across conductors 610 and 598, provide an adjustably selected voltage value to be also applied to input terminal 6. An N-P-N transistor 628 has its base 630 connected to the output terminal 7 of amplifier through resistance means 640 while its emitter 642 is connected to common conductor means 596 and the collector 644 is in series with heater means 78 and 92 and conductor means 598.

The heater and regulating means is provided in order to prevent the temperature of the R-LED 68 and/or the phototransistor 66 from decreasing to a value which would cause impairment of the operation thereof. Accordingly, when the temperature drops to a predetermined value, as determined by the setting of potentiometer means 608, an output is generated on conductor 616 and applied to input terminal 5 of amplifier and, if such input signal exceeds the reference value established by the selective adjustment of potentiometer 626, an output is producied at terminal 7 sufficient to turn transistor 628 on thereby passing current through the heater means 78 and 92. The system is a closed loop since as the heater heats, for example, the R-LED 68, the linearly responsive temperature sensing means 80 monitors the temperature of the R-LED 68 thereby affecting shut-off of the transistor 628 upon attaining a sufficient increase in temperature and an attendant reduction in the magnitude of the signal applied to input 3 of amplifier 592.

Figure 10:
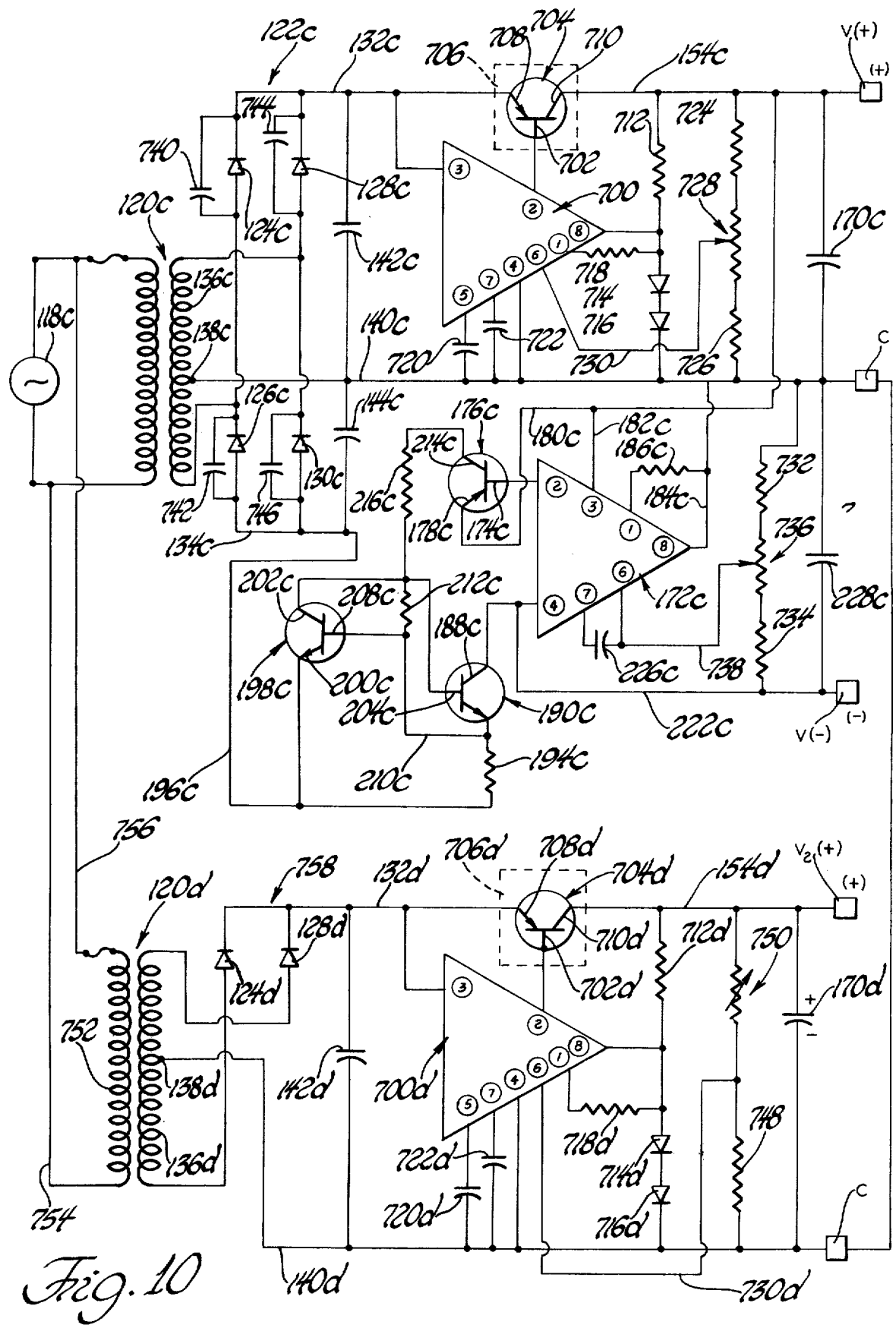
FIG. 10 is a schematic wiring diagram of another regulated power source employable in practicing the invention.

FIG. 10 illustrates another power supply means employable, as for example, with the other embodiments of the invention disclosed in FIGS. 11, 12, 13 and 14. Such elements in generally the upper two-thirds of FIG. 10 as are like or similar to those of FIG. 3 are identified with like reference numbers provided with a suffix C.

In FIG. 10 an amplifier 700 has its terminal 3 connected to conductor 132c and its terminal 2 connected to the base 702 of a P-N-P transistor 704 which, as schematically shown, is in heat sink relationship to suitable heat sink chasis means 706. The emitter 708 and collector 710 of transistor 704 are respectively connected to conductor means 132c and 154c. A resistor 712, in series with diode means 714 and 716 is placed across conductors 154c and 140c while terminals 8 and 1 of amplifier 700 are each connected as to a point between said resistor 712 and diodes 714, 716 with terminal 1 being thusly connected through resistor means 718. Terminals 5 and 7 of amplifier 700 are respectively connected, through capacitors 720 and 722, to common conductor 140c. Potentiometric voltage dividing network means comprising resistor means 724 and 726 and potentiometer means 728 is placed across conductor means 154c and 140c has its potentiometer means 728 connected to amplifier terminal 6 via conductor means 730. Similar potentiometric voltage dividing network means, placed across conductors 140c and 222c comprises resistor means 732 and 734 and potentiometer means 736 which via conductor means 738 is connected to amplifier 172c terminal 6 and through capacitor 226c to amplifier terminal 7. Further, as indicated, capacitors 740, 742, 744 and 746 are preferably placed in parallel with rectifier diodes 124c, 128c and 130c.

The lower third of FIG. 10 functionally corresponds generally to the purpose and function of the circuitry of FIG. 4 in that it provides a regulated power source for the thermocooler 56. Those elements in the lower third of FIG. 10 which are like or similar to elements of the upper two-thirds of FIG. 10 are identified with like reference numbers provided with a suffix d. As shown, terminal 6 of amplifier 700d is connected as to a point between resistor 748 and series potentiometer 750 which, across conductors 154d and 140d, comprise a potentiometric voltage dividing network. The primary winding 752 of transformer means 120d may be connected electrically across source 118c as by conductor means 754 and 756. As should be apparent, the dioded 124d and 128d, comprising rectifier means 758, provide for half-wave rectification and that the regulated d.c. output across conductors 154d and 140d is produced by such half-wave rectification.

Figure 11:
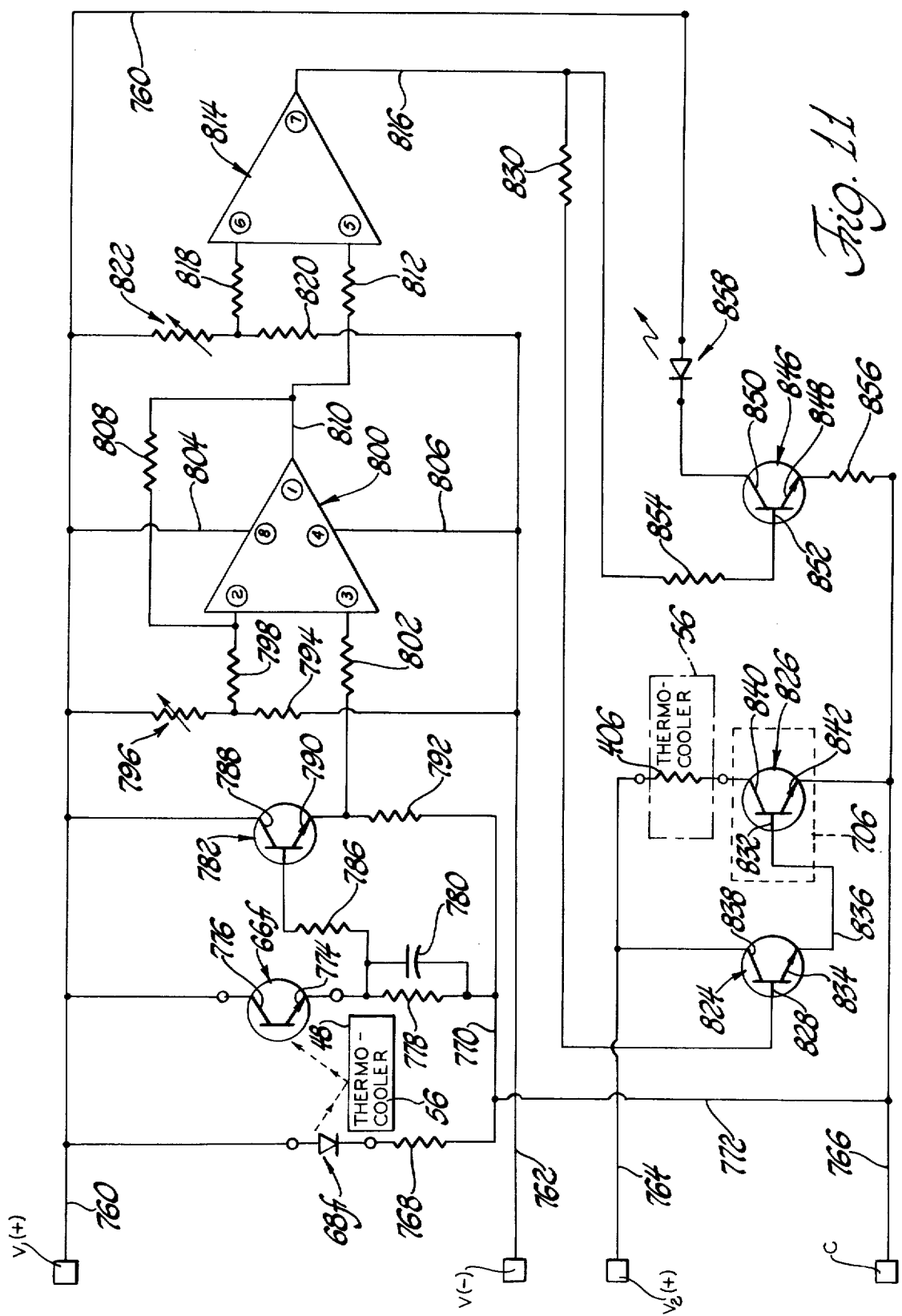
FIG. 11 is a schematic wiring diagram of another embodiment of the invention for determining the dew point temperature.

Referring now in greater detail to FIG. 11, the main conductors 760, 762, 764 and 766 are respectively adapted for electrical connection as to conductors 154c, 222c, 154d and 140c or 140d of FIG. 10 as to thereby be respectively at the indicated potentials V(+), V(−), $V_s$(+) and C.

In the embodiment of FIG. 11, the infrared light emitting diode 68f (functionally equivalent to, for example, diode 68b of FIG. 8) is connected, as in series with current limiting resistance means 768, across conductors 760 and 770 which, in turn, is connected to common conductor means 766 via conductor means 772. A phototransistor 66f (functionally equivalent to, for example, phototransistor 66b of FIG. 8) is similarly connected, as by havings its emitter 774 and collector 776 in series with resistance means 778, across conductors 760 and 770. Capacitor means 780 is placed in parallel with resistance means 778 while the base 784 of an N-P-N transistor 782 is connected through resistance means 786 to emitter 774 of transistor 66f. The collector 788 of transistor 782 is connected to conductor means 760 while emitter 790 thereof is connected as through resistor 792 to conductor means 770 and 766.

A potentiometric voltage dividing network, comprising resistor means 794 and polentiometer means 796 is connected across conductor means 760 and 762 and also connected via resistance means 798 to an input terminal 2 of an amplifier 800. The positive input terminal 3 of amplifier 800 is electrically connected, as through resistance means 802, to emitter 790 of transistor 782. Amplifier 800 terminals 8 and 4 are respectively electrically connected to potentials V(+) and V(−) as by means of conductors 760 and 762 and as through conductors 804 and 806, while the output at terminal 1 is fed back to negative input terminal 2 through resistance means 808.

The output from terminal 1 of amplifier 800 is also applied via conductor means 810 and resistance means 812 to the positive input terminal 5 of a comparator 814 which, for purposes of description, may be considered as providing a switching function to the output on conductor means 816 at its terminal 7. The negative input terminal 6 is connected as through resistance means 818 to a point as between resistance means 820 and potentiometer means 822 comprising a potentiometric voltage divider network across conductors 760 and 762.

A pair of N-P-N transistors 824 and 826 are arranged as to have the base 828 of one connected to conductor 816 as through resistor 830 and the base 832 of the other connected to the emitter 834 of the first transistor 824 as through conductor means 836. The collector 838 of transistor 824 is electrically connected to conductor means 764 as is one terminal of the P-N junction device 406 of thermocooler 56. The other terminal of P-N junction device 406 is connected to collector 840 of transistor 826 while the emitter 842 thereof is connected to conductor means 766.

A third N-P-N transistor 846, having an emitter 848, collector 850 and base 852 is electrically interconnected as to have its base 852 in series circuit with conductor means 816 and resistor 854 while the emitter 848 is connected to conductor means 766 through resistor means 856. Suitable output means, such as a light emitting diode 858, is connected in series with V(+), as through conductor means 760, and collector 850 of transistor 846.

In operation, the continuous d.c. energization of diode 68f causes infrared energy to be directed therefrom and against the surface 48 of thermocooler 56 from where such infrared energy is reflected, in the absence eof either moisture or frost on surface 48, at phototransistor 66f causing the phototransistor 66f to be on and conductive thereby resulting in a relatively high voltage drop across resistor means 778. Generally, the phototransistor 66f functions as an emitter follower.

When dew, moisture or frost is present on surface 48 of thermocooler 56, at least a substantial amount of the infrared energy from diode 68f is absorbed thereby thusly causing phototransistor 66f to be either turned off or at least significantly reduced in its conductivity thereby reducing the voltage drop across resistance means 778 as to, for example, only a small fraction of the voltage drop occurring thereacross during absence of moisture or frost.

Transistor 782 follows the voltage drop across resistance 778 and serves to inter-phase as to, in effect, assure that the voltage developed across resistance means 778 is generally isolated and not adversely effected by other devices which may be environmentally associated therewith.

The output from buffer transistor 782 is applied to amplifier 800 input terminal 3 while the potentiometer 796 is adjusted as to select the desired operational range of amplifier 800. Generally, potentiometer 796 is adjusted in a manner so that, preferably, as a change in condition from, for example, the presence of dew or frost to the absence of dew or frost is sensed, the amplifier will have a maximum swing or range of voltage.

Potentiometer 822 is, in turn, adjusted as to thereby determine a reference voltage value at which the comparator 814 will switch off. The output of comparator 814 is applied via conductor means 816 to transistors 824 and 826, which comprise a Darlington type network, causing transistor 826 to be turned on and off depending on whether, respectively, there is the presence of dew, moisture or frost, or there is the absence of dew, moisture or frost.

Of course, the transistor 826 will be on causing the surface 48 of thermocooler 56 to continually cool until moisture does form on surface 48 which then establishes, for those atmospheric conditions, the dew point or temperature of the condensation ambient. When such moisture is thusly caused to precipitate on surface 48, the voltage across resistor 778 drops and, as previously indicated, transistor 826 is turned off thereby permitting the heat in the thermocooler 56 previously driven toward or to sink to flow in the reverse direction to thereby heat surface 48 and evaporate the moisture thereon. The transistor 826 will thusly cylce "on-and-off" at that particular dew point thereby establishing an actual reading of the dew point. At the same time, the same output from comparator 814 causing the cyclic on-and-off of transistor 826 also causes the same cyclic on-and-off turning of transistor 846 which, in turn, causes the same cyclic energization and de-energization of output device 858 which, as illustrated, may be a light emitting diode even though not necessarily limited thereto. The device 858 is provided mainly as indicating means to indicate, as by visual and/or auditory signal means, that the thermocooler and related circuitry of FIG. 11 are operating. Even though the light emitting diode means 858 is preferred, other indicating means may of course be employed.

Figure 12:
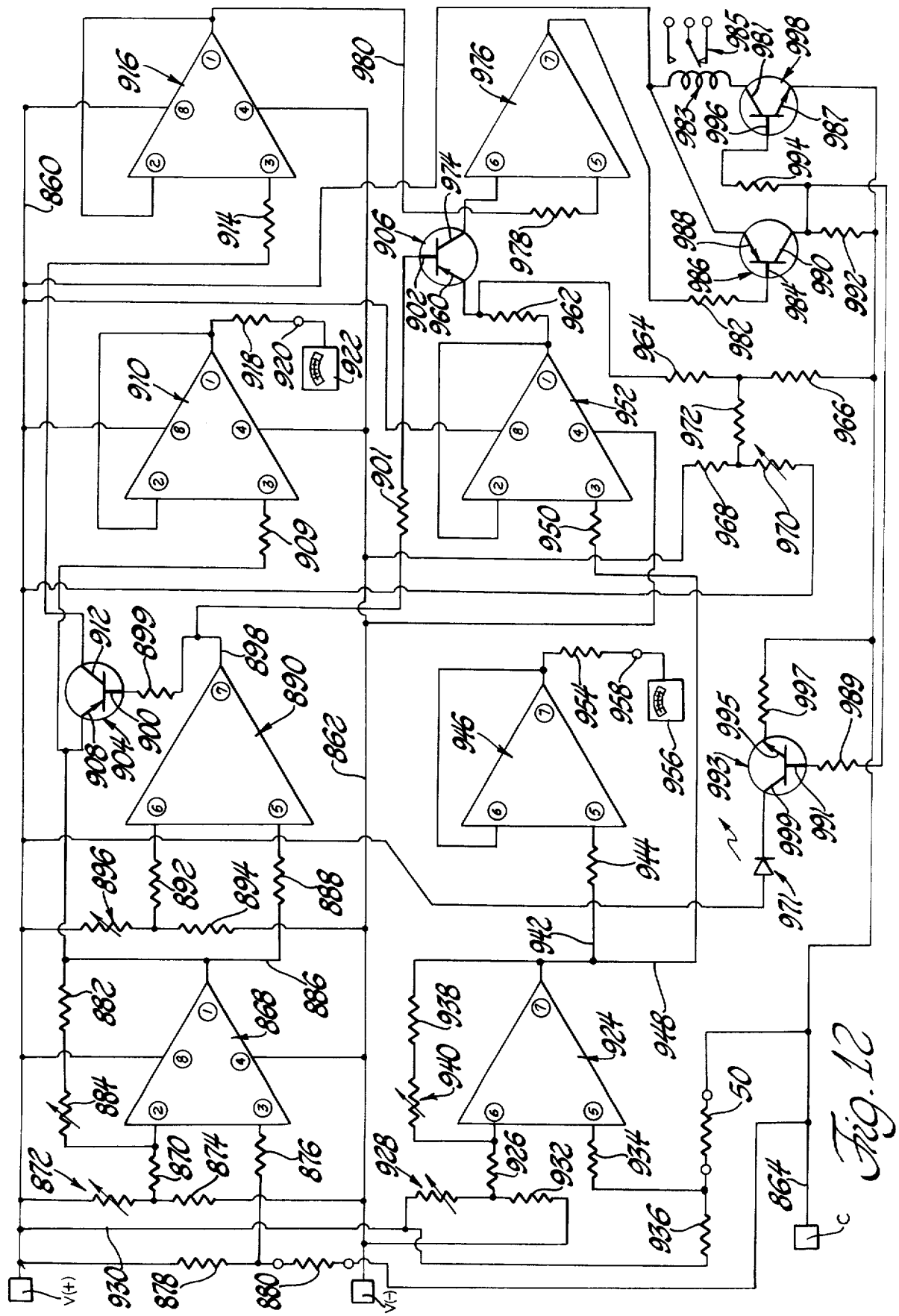
FIG. 12 is a schematic wiring diagram of circuitry employable, for example, in combination with the circuitry of FIG. 11 for sensing additional parameters and in response thereto producing selected outputs.

FIG. 12 schematically illustrates the temperature sensing, comparison and switching circuits employed in combination as with the circuitry of FIGS. 10 and 11.

Referring in greater detail to FIG. 12, main conductor means 860, 862 and 864 are respectively connected to terminal or conductor means at relative potentials V(+), V(−) and C which, of course, may be electrically connected to, for example, conductors 154c, and 222c and 140c of FIG. 10. The negative terminal 2 of a first amplifier 868 is connected as through resistance means 870 to a point generally between a potentiometer 872 and resistance means 874 forming a potentiometric voltage divider network across conductors 860 and 862. The positive input terminal 3 of amplifier 868 is similarly connected via resistor 876 to a record voltage divider, across conductor means 860 and 864, comprising a resistor 878 and linearly responsive and variable temperature responsive resistance means 880 situated as to be in heat transfer relationship to the ambient or, if desired, to a particular actual surface being monitored. Amplifier 868 terminals 8 and 4 are respectively electrically connected to the relative potentials of conductor means 860 and 862 while the output from terminal 1 thereof is fed back to terminal 2 thereof as by resistance means 882 and 884 with resistor 884 being preferably adjustable as to thereby be able to selectively adjust the gain of amplifier 868.

The output from terminal 1 is applied as via conductor means 886 and resistance means 888 to the positive input terminal 5 of a comparator 890 which has its negative input terminal 6 connected, via resistance means 892, to a potentiometric voltage divider network, across conductors 860 and 862, comprised of resistor means 894 and potentiometer 896. The output from terminal 7 of comparator 890 is applied to conductor means 898 as to thereby be applied through resistors 899 and 901 to the base terminals 900 and 902 of respective P-N-P transistors 904 and 906. The emitter 908 of transistor 904 is electrically connected to output terminal 1 of amplifier 868 and through resistance means 909, to the positive input terminal 3 of an amplifier 910 which has its terminals 8 and 4 respectively connected to conductors 860 and 862. The collector 912 of transistor 904 is electrically connected through resistance means 914 to the positive input terminal 3 of a buffer amplifier 916 which also has its terminals 8 and 4 respectively connected to conductors 860 and 862. The outputs of both amplifiers 910 and 916 are respectively fed back to the respective negative input terminals 2 of each of such amplifiers. The output from amplifier 910 applied as through calibrating resistance means 918 to suitable terminal means 920, may be read directly as by voltmeter means 922 plugged into such terminal means 920 to thereby obtain a direct reading of the monitored ambient or surface temperature as sensed by means 880. If, for example, the system is so adjusted, originally, that a 0 output at terminal 1 of amplifier 910 indicates freezing temperature (32° F) then, because of the use of a common conductor at a relative potential C, it becomes possible to read directly from the voltmeter means 922 as to whether the monitored ambient or surface temperature is below or above freezing (32° F) merely by whether the voltmeter reads a positive (+) or negative (−) value.

As previously explained with reference to the other embodiments, the various temperature references and off-sets can be whatever values are desired. Accordingly, as previously also assumed for purposes of illustration and discussion, let it be assumed that potentiometer 896 has been so adjusted as to cause the output at terminal 7 of amplifier 890 to be 0 when the temperature actually sensed by temperature sensing means 880 is 32° F.

Still referring to FIG. 12, an amplifier 924 has its negative input terminal 6 connected via resistor 926 to a potentiometric voltage divider network comprised of a potentiometer 928 electrically connected, as by conductor means 930, to conductor 860 at V(+), and resistance 932 electrically connected to conductor means 862 at V(−). The positive input terminal 5 of amplifier 924 is electrically connected through resistance means 934 to a second voltage divider network, across conductors 860 and 864, comprised of resistance means 936 and linearly responsive and variable temperature responsive resistance means 50 situated as to be in heat transfer relationship to surface 48 of thermocooler 56 so as to be continually responsive to the actual temperature of such surface 48. The output from terminal 7 of amplifier 924 is fed back to input terminal 6 as by resistance means 938 and 940 with resistance 940 being preferably adjustable as to thereby be able to selectively and closely adjust the gain of amplifier 924. Potentiometer 928 is adjusted in order to create the necessary off-set to the signal generated by the temperature responsive means 50 in order to thereby establish the desired temperature reference. The output at terminal 7 of amplifier 924 is, via conductor means 942 and resistance means 944 applied to the positive input terminal 5 of an operational amplifier 946, and, via conductor means 948 and resistance means 950 applied to the positive input terminal 3 of an amplifier 952. The output at terminal 7 of amplifier 946 is fed back to the negative input terminal 6 while the output at terminal 1 of amplifier 952 is similarly fed back to its negative input terminal 2. Further, the output from amplifier 946, applied as through calibrating resistance means 954 to suitable terminal means 958, may be read directly as by voltmeter means 956 plugged into such terminal means 958 to thereby obtain a direct reading of the dew point temperature sensing means 50. If, for example, the system is so originally adjusted that a 0 output at terminal 7 of amplifier 946 indicates a selected freezing temperature (32° F for example) then, because of the use of a common ground or conductor at a relative potential C, it becomes possible to read directly from the voltmeter means 956 as to whether the dew point temperature is below or above the said freezing temperature merely by whether the voltmeter reads a positive (+) or negative (−) value.

Terminals 8 and 4 of amplifier 952 are respectively connected to conductor means 860 at a reference of V(+) and to conductor means 862 at a reference of V(−) while the output from terminal 1 thereof is applied to emitter 960 of transistor 906, through resistance means 962. Emitter 960 is also connected to one end of a voltage dividing network, comprised of resistance means 964 and 966, the other end of which is connected to conductor means 864 at a potential C. A record voltage divider, comprising resistance means 968 and potentiometer 970, is connected across conductors 860 and 862 and further connected as by resistor 972 to the network comprised of resistors 964 and 966.

The collector 974 of transistor 906 is connected to the negative input terminal 6 of an amplifier 976 while the positive input terminal 5 thereof is connected through resistance means 978 to the output terminal 1 of amplifier 916 via conductor means 980.

The output of amplifier 976 is applied through resistance means 982 to the base 984 of a P-N-P transistor 986 which has its emitter 988 connected to conductor 860 at V(+) and its collector 990 connected through resistor 992 to common conductor means 864 at C. The collector 990 is also connected through resistance means 994 to the base 996 of an N-P-N transistor 998 having its collector 981 connected as to one side of, for example, a relay winding 983, effective to control relay switch means 985, and having its emitter 987 connected to common conductor 864. The other end of relay winding 982 is connected to conductor means 860 at V(+). The collector 990 of transistor 986 may be connected through resistance means 989 to the base 991 of yet another N-P-N transistor 993 having its emitter w95 connected to conductor 864 through resistance means 997 and its collector 999 in circuit with a light emitting diode 971 the other end of which is connected as to conductor 860 at V(+).

Until the signal from the ambient or monitored surface temperature sensing means 880 reaches the value or temperature to which amplifier 890 is oriented to (assumed to be 32° F), there will be no actuating output from output terminal 7 of comparator 890. Once the sensed ambient temperature reaches a value to which comparator amplifier 890 is set for, or below that value, comparator 890 switches and creates an output causing transistor 904 to turn on and become conductive thereby passing the output signal from output terminal 1 of amplifier 868 through its emitter 908 and collector 912 to the input terminal 3 of buffer amplifier 916. At this same time the output of terminal 1 of amplifier 916 is applied to the positive terminal 5 of amplifier 976. Accordingly, amplifier 976 thusly obtains an input signal thereto of a value indicative of the sensed ambient, or monitored surface, temperature.

During this time the dew point temperature signal from amplifier 924 fed to and buffered by amplifier means 952 is passed through the emitter 960 and collector 974 of transistor 906 (which has been turned on by amplifier 890 at the same time that transistor 904 was turned on) to the other input terminal 6 of amplifier 976. At this point it should be apparent that both transistors 904 and 906 will be either on or off depending upon the output of amplifier 890 and whether the sensed temperature by means 880 is above or below the value of the freezing reference temperature. If the sensed temperature is above the freezing reference temperature, both transistors 904 and 906 will be off.

If amplifier 976 senses no inputs at its input terminals 6 and 5, its output will be relatively high thereby causing transistor 986 to be held off which, in turn, keeps transistor 998 off so as to prevent current flow through related output means such as, for example, at 983 and 985. This would, of course, indicate a non-icing or safe operating condition.

When both transistors 904 and 906 are turned on, the inputs applied to amplifier 976 cause the output at terminal 7 of amplifier 976 to decrease in magnitude permitting transistors 986 and 998 to turn on as to thereby cause energization of any desired related warning, control or corrective means as exemplified by the relay means 983 and 985.

Potentiometer 970 provides for adjustment means whereby it becomes possible to alter the magnitude or value of the signal from amplifier 952 as to create a desired differential with reference to the actual sensed dew point temperature to thereby enable the system, at amplifier 976, to create an output even if there might be, for example, a few degrees difference between the referenced freezing temperature and the sensed dew point temperature.

Further, transistor 993 and diode means 971 are shown to illustrate that other, possibly remotely situated, means may be provided and energized cotemporaneously to create signal means indicating that, for example, icing conditions exist.

Figure 13:
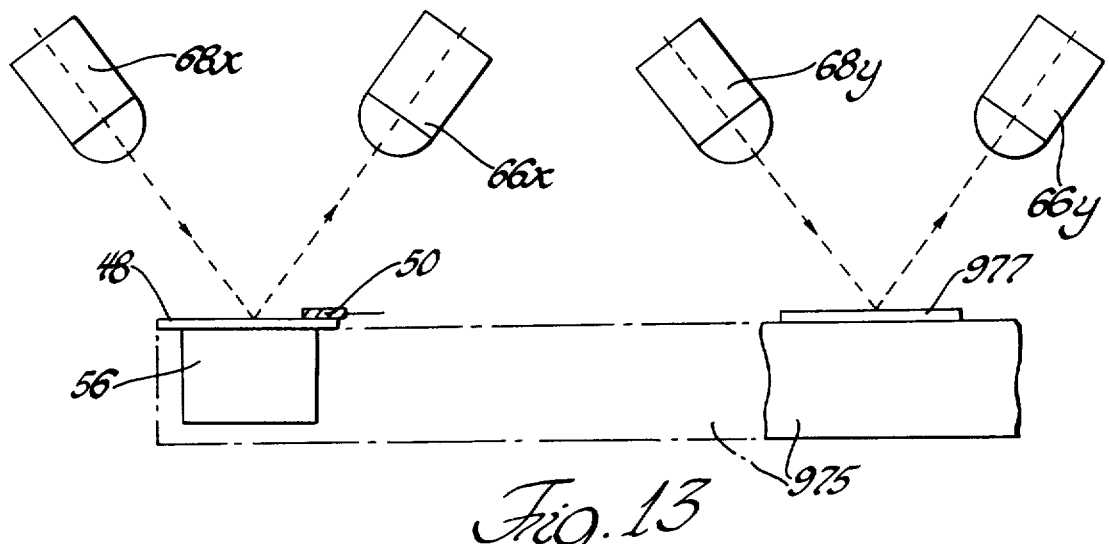
FIG. 13 is a simplified generally elevational view of means similar to that shown in FIG. 2 but, in the main, employing two pairs of light emitting diodes and phototransistors.
Figure 14:
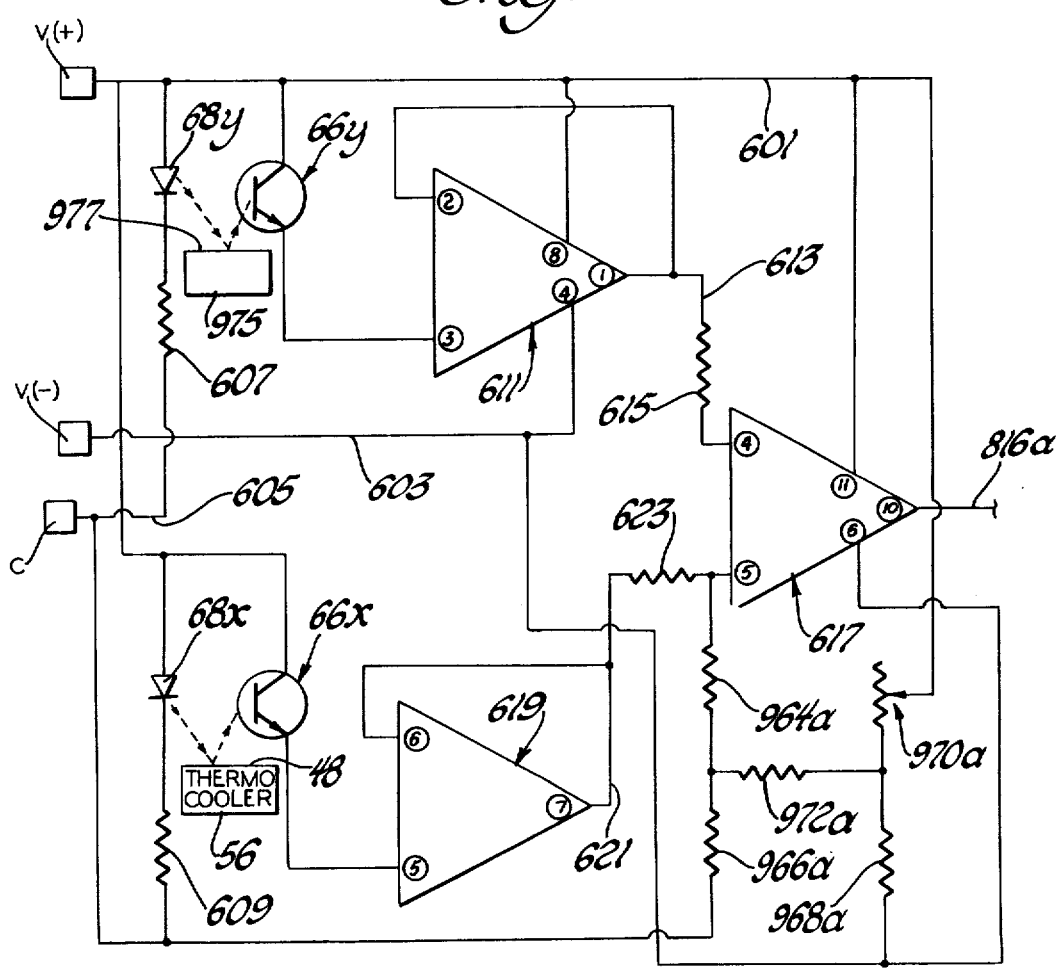
FIG. 14 is a schematic wiring diagram fragmentarily illustrating an embodiment of the invention employing the structure generally depicted in FIG. 13.

FIGS. 13 and 14 contemplate other embodiments of the invention. FIG. 13 is shown in simplified form. That is 68x is an infrared light emitting diode functionally equivalent to, for example, 68 of FIG. 2, 66x is a phototransistor functionally equivalent to, for example, 66 of FIG. 2, 68y is an infrared light emitting diode functionally equivalent to, for example, 68 of FIG. 2; and 66y is a phototransistor functionally equivalent to, for example, 66 of FIG. 2.

As in FIG. 2, with many of the elements and details shown therein not being here repeated, a theremocooler 56 has a reflective surface 48 from which the radiation of R-LED 68x is reflected to impinge on phototransistor 66x. A suitable temperature responsive and sensitive means as 50 of FIG. 2 is shown on reflective thermocooler surface 48. The thermocooler 56 may be suitably carried or supported by heat sink type housing means 975 which also carries a second reflective surface means 977 which, however, is not in any way acted upon, temperaturewise, by the thermocooler 56. The second coacting pair of infrared light emitting diode 68y and phototransistor 66y are situated with respect to the second reflective surface 977 in the same manner as are 68x and 66x with respect to thermocooler reflective surface 48.

With reference to FIG. 14, it can be seen that each of the R-LED diodes 68y and 68x are connected at one end to conductor means 601 leading to voltage V(+) and that they are also connected, through respective resistors 607 and 609 to the common ground conductor means 605 leading to C, while the collectors of each of the phototransistors 68x and 66x are connected to V(+) of conductor means 601.

An amplifier 611 has its positive input terminal 3 connected to the emitter of phototransistor 68x while the output at terminal 1 thereof is fed back to the negative input terminal 2. The amplifier 611 terminals 8 and 4 are respectively connected to conductor means 601, at V(+), and 603 at V(−). The output from terminal 1 of amplifier 611 is applied via conductor means 613 and resistance means 615 to the negative terminal 4 of a comparator 617 which has its terminals 11 and 6 respectively electrically connected to conductor means 601 and 603.

Similarly, the emitter of phototransistor 66x is connected to the positive input terminal 5 of an amplifier 619 which has its output at terminal 7 fed back to the negative input terminal 6. Further, the output of amplifier 619 is applied on conductor means 621 and resistance means 623 to the positive input terminal 5 of comparator 617. Resistance means 964a, 966a, 972a, 968a and 970a respectively correspond to means 964, 966, 972, 968 and 970 disclosed in and described with reference to FIG. 12. Further, generally, comparator 617 would function in the system as does amplifier 814 of FIG. 11 in that the output conductor means 816a of FIG. 14 would correspond directly to the output conductor means 816 of FIG. 11.

Referring to both FIGS. 13 and 14, infrared diode 68x and phototransistor 66x, as a pair, may be considered as the sensing photo-optics. The other pair of infrared diode 68y and phototransistor 66y are focused on an identical reflective surface 977 also generally contained by the overall housing means, but without any cooling means therefor. At this point it might be mentioned that surface 48, in all embodiments may, in the preferred form, be either white or black and, of course, the same applies to surface 977 which should correspond. Such second set of 68y and 66y may be referred to as the compensating and reference photo-optics. As shown in FIG. 14, the respective outputs of phototransistors 66x and 66y are applied to inputs of respective amplifiers 619 and 611. As the thermocooler 56 cools the reflective surface 48, dew or frost will appear on such surface 48 as it reaches the dew point temperature. At this point the moisture on the cooled reflective surface 48 nearly completely absorbs the infrared energy from diode 68x thereby causing de-energization and non-conduction of phototransistor 66x. As a result, the operational amplifier 617 experiences a proportional signal drop at one of its inputs while the signal level at the other of the inputs is maintained at a relatively high value or magnitude by the reference photo-optics 68y and 66y. Consequently, the operational amplifier 617 switches to a negative value or to its off state thereby turning off the current supply to the thermocooler, as discussed, for example, with reference to FIG. 11. With the cooling cycle to the surface 48 being thusly terminated, heat reversal occurs and surface 48 starts to become warmed by the heat flow from the associated heat sink means. As already discussed with reference to prior embodiments, at a specific point the dew will disappear from the reflective surface 48 (depending on the actual dew point) and phototransistor 66x will again receive the reflected infrared energy due to the absence of moisture on surface 48, causing, in turn, the next cooling cycle to start thereby again lowering the temperature of surface 48 to the dew point. During the cyclic event, the temperature of the reflective surface 48 is monitored thereby obtaining the true dew point temperature.

The compensating photo-optics 66y and 68y along with the non-cooled surface 977 serve as a floating reference for the operational amplifier 617 and also serve as surface contamination and temperature compensating means. That is, since both surfaces 48 and 977 will be presented to the same ambient, their surface conditions, especially relative to accumulation of any dirt thereon, should be for all practical purposes identical.

In addition to the other benefits derived from the embodiment of FIGS. 13 and 14, it should be apparent that the parallel arrangement of the pairs of infrared light emitting diodes and phototransistors automatically provides for a "floating" reference even for variations in operating characteristics of such diodes and phototransistors due to, for example, an increase in the operating temperatures thereof (sometimes referred to as "temperature drift").

As should be apparent, the various embodiments and modifications of the invention disclosed herein provide means whereby any desired surface of any desired structure can be readily and accurately monitored in either a direct mode or in an anticipating mode for dew and/or frost formation. The invention also provides means for being able to accurately monitor and, if desired, anticipate frost and/or icing conditions in any gas atmosphere, as for example, the monitoring of natural gas flowing within pipe-lines. The invention is also capable of having a plurality of signal inputs such as dew point, ambient (whether atmospheric or a closed atmosphere of other gas or gases) temperature, monitored surface temperature from which to select as either primary or secondary signal values to which response will be made depending on the order of importance assigned to such signals.

Further, depending on the requirements of the physical package in which the infrared diode and the phototransistor are to be contained, the invention can be practiced by pulsing the infrared diode to very high energy levels thereby being able to accommodate relatively long reflective distances as between the infrared diode, the reflecting surface and the phototransistor while where such reflective distances are relatively short, the infrared diode can be operated at a steady stated d.c. mode at energy levels well within the limits of its normal operating characteristics.

Only for purposes of further detailed disclosure and not be way of limitation, the following commercially available components were employed in the construction of various successful embodiments of the invention as generally hereinafter set forth.

For example, in FIGS. 3 and 4, amplifiers 146, 172, 146a and 172a were each RCA solid state positive voltage regulators No. CA3085 as appear, for example, in the "RCA Linear Integrated Circuits and DMOS Devices" databook No. SSD-201C copyright 1974 by RCA Corporation having offices at Summerville, New Jersey; transistors 230, 232, 234, 236 and 238 of FIG. 5 were each Motorola transistors No. 2N4124 as identified in, for example, the publication "Motorola Semiconductor Data Library" dated 1973 and published by Motorola Semiconductor Products, Inc. having offices in Phoenix, Ariz.; the various amplifiers 346, 348, 350 and 352 of FIG. 5, the amplifiers 450, 420, 474, 426 and 500 of FIG. 6, the amplifiers 526, 520, 568 of FIG. 7, and the amplifiers 346b, 592 and 612 of FIGS. 8 and 9 were each Fairchild solid state amplifiers No. MC-1458 as disclosed, for example, in the publication "Fairchild Linear Integrated Circuit Data Catalog" dated 1974, and published by Fairchild Semiconductor Company having offices at 313 Fairchild Drive, Mountain View, Calif.

The linear resistors, such as 50 of FIG. 6 and/or 454 of FIG. 6 and/or 530 of FIG. 7, and/or 80 of FIG. 9 and/or 872 and 928 of FIG. 12 were Minco "RTD's" various sizes of which appear in "Bulletin No. TR-2", dated 1974, and published by Minco Products, Inc. having offices at 7300 Commerce Lane, Minneapolis, Minn.; the heater element such as at 78 of FIG. 2 was a Minco Heater No. HR-5072 as appears in "Bulletin No. TF-4" dated 1974, and published by said Minco Products, Inc.; and the operational amplifiers 800, 814, 868, 890, 910, 916, 924, 946, 952 and 976 of FIGS. 11 and 12 were each Fairchild amplifiers No. MC-1458 as disclosed, for example, in the publication "Fairchild Linear Integrated Circuit Date Catalog," dated 1974 and published by Fairchild Semiconductor Company having offices at 313 Fairchild Drive, Mountain View, Calif.

As is well known in the art, the various terminal numbers of the various amplifiers, comparators and regulators referred to herein relate to the terminal numbers as are published and/or understood in the art as designating particular terminal points of such solid state devices for achieving the internal connections and thereby attaining the desired circuitry to perform the functions recited.

The specific circuitry disclosed herein may be modified of course with the use of other components without in any way departing from the spirit of scope of the invention. For example, there may be a direct substitution of an injection laser for the infrared light emitting diode. An injection laser, of course, being a semiconductor device which is capable of emitting coherent light energy in a broad spectrum which includes the infrared portion thereof. Such would be of exceptional benefit in situations where very high emitted energy levels would be required in a very concentrated beam. For example, such would be to definite advantage where the environment or atmosphere was highly explosive and the infrared light emitting source would have to be spaced a long distance from the gauging surface which would be located within the atmosphere. Further, with a very concentrated light beam, it would be possible to strike and reflect off the gauging surface at a very small selected point thereof especially where it would be desired or required that the presence or absence of dew be sensed at a very small "pin-point" like area of the gauging surface.

Also, it is possible to employ a pin photodiode in place of the phototransistor. As is known, a pin photodiode is, generally, as any other diode except that among other things, it has a very small sensing optical area which usually requires greater energy input levels but as a consequence has an extremely fast "turn-on" or response time. In such instance, the pin photodiode could be employed in combination with either the infrared light emitting diode or the injection laser. The use of a pin photodiode provides increased benefits such as, for example, decreases the response time of the system in that the response time of the pin photodiode is very much faster than that of the phototransistor. Another advantage is that such pin type photodiode will respond to a very narrow width of a light beam. Accordingly, it should be clear that both in the disclosure and claims the term phototransistor also comprises a photodiode and that the term photodiode also comprises a phototransistor since their functions within the overall invention are the same.

Also, in view of the teachings and disclosure herein made, it becomes possible to employ the inventive concepts in other environments and for other purposes. That is, as clearly disclosed, dew and/or frost deposited on, for example, the gauging surface 48 will function to absorb infrared energy. Further, as discovered and explained by way of background to the invention, two of the factors influencing the degree of infrared energy absorption is the concentration of the dew or frost deposit and the thickness of the layer of such dew or frost. Accordingly, the invention as herein presented is capable, by selective adjustment of the circuit components or circuit constants, of producing desired output signals when a particular preselected concentration and/or thickness of dew and/or frost is sensed on the related gauging surface. The invention has been disclosed and discussed in terms of what might be considered the instantaneous detection of the mere instantaneous presence of dew and/or frost; however, it should be clear that no changes to the disclosure as such is necessary in order to enable one of even ordinary skill in the art to employ the invention in a mode of operation based on either concentration or thickness of dew and/or frost.

Further, it should be apparent that even though the invention has been disclosed and discussed in terms of detecting the dew point temperature of an atmosphere (closed gas or ambient) carrying a vaporized liquid in suspension, the invention as disclosed is able to be practiced in environments which do not include the problem of determining either dew point temperatures of any atmosphere or the use of thermocooler means.

For example, referring to FIG. 15, it is possible to provide a light beam emitting source 1,000 such as infrared light emitting diode 68 and a photosensitive device 1,002 such as phototransistor 66 and position then, as generally described with reference to FIG. 2 but now with respect to, for example, a moving member 1,004 which, in fact, may be suitable strip stock material which is exiting from suitable related apparatus 1,006. If it is assumed that the apparatus 1,006 is the type which applies a coating to the material 1,004, then devices 1,000 and 1,002 would employ the surface 1,008 in the same way as surface 48 of thermocooler 56 or surface 977 of member 975 (of FIG. 14) were employed, namely, as a reflecting and/or gauging surface. Devices 1,000 and 1,002 would then function to determine, for example, if the proper thickness or concentration of the assumed coating was applied and very possibly create feed-back signals to related control means for assuring the application of a proper coating. If it is assumed that the apparatus 1,006 is the type which serves to dry a coating previously applied at a separate work station and that such drying is accomplished as said material 1,004 passes through apparatus 1,006, then devices 1,000 and 1,002 (with of course the related circuitry) could serve to detect whether such drying operation was completed and provide feedback signals corresponding to the detected condition.

Although only a select number of preferred embodiments and modifications of the invention have been disclosed and described, it is apparent that other embodiments and modifications of the invention are possible within the scope of the appended claims.

I claim:

1. Apparatus for determining the dew point temperature of a vaporized liquid carried within a gas atmosphere, comprising a test surface to be situated within said gas atmosphere, first means for controllably varying the temperature of said test surface, said first means being effective during a first phase of operation for cooling said test surface sufficiently to cause said vaporized liquid within said gas atmosphere to come out of suspension and precipitate as a dew upon said cooled test surface, said first means being effective during a second phase of operation for heating said test surface as to thereby vaporize from said test surface any formation thereon of said dew, second means for continually sensing the temperature of said test surface and effective for continually producing a temperature output signal in response thereto, and indicating means responsive to the formation of said dew upon said cooled test surface, said indicating means being effective upon sensing the said formation of said dew to terminate said first phase of operation and further cooling of said test surface and to initiate said second phase of operation and thereby heat said test surface and remove said formation of said dew therefrom, said indicating means being effective to cyclically initiate said first phase of operation upon the absence of said formation of said dew and being effective to initiate said second phase of operation upon the occurrence of said formation of said dew to thereby generally substantially stabilize the magnitude of the then existing temperature of said test surface thereby resulting in said stabilized magnitude of temperature being said dew point temperature, said indicating means comprising photo-optic means, a light source effective for directing a beam of light against said test surface at an angle as to have said beam of light reflect from said test surface and impinge upon said photo-optic means during both said first and second phase of operation, said beam of light being the only source of actuating light energy conveyed to said photo-optic means.

2. Apparatus according to claim 1 wherein said test surface comprises thermocooler means.

3. Apparatus according to claim 1 wherein said means for continually sensing the temperature of said test surface comprises linear coefficient temperature responsive electrical resistance means situated in heat transferance relationship to said surface means.

4. Apparatus according to claim 1 wherein said photo-optic means is sensitive to the change in the energy level of said light energy of said beam of light reflected from said test surface during the absence of said dew thereon and the same beam of light reflected from said test surface when said dew is present on said test surface.

5. Apparatus according to claim 4 wherein said light source is cyclically energized and de-energized as to cause said beam of light to be cyclically pulsed against said test surface and to be accordingly reflected from said test surface in a cyclically pulsed manner.

6. Apparatus according to claim 1 wherein said test surface comprises thermocooler means, wherein said means for continually sensing the temperature of said test surface comprises linear coefficient temperature responsive electrical resistance means situated in heat transfer relationship to said test surface, and wherein said photo-optic means is sensitive to the change in the energy level of said light energy of said beam of light reflected from said test surface during the absence of said dew thereon as compared to the same said beam of light reflected from said test surface when said dew is present on said test surface.

7. Apparatus according to claim 1 wherein said beam of light comprises a beam of infrared light, wherein said light source comprises infrared diode means, wherein said photo-optic means comprises phototransistor means, said infrared diode means being effective to generate and direct said beam of light against said test surface as to thereby cause said beam of light to reflect from said test surface and onto said phototransistor means, said reflected beam of infrared light being of sufficient energy to cause said phototransistor means to go into conduction when said dew is not present on said surface means, and said reflected beam of light being of insufficient energy to cause said phototransistor means to go into conduction when said dew is present on said surface means, the difference in energy between said sufficient energy and said insufficient energy being due to absorption of infrared energy by said dew.

8. Apparatus according to claim 7 wherein said test surface comprises thermocooler means, and wherein said phototransistor means when not conducting is effective to de-energize electrical energization of said thermocooler means.

9. Apparatus according to claim 1 wherein said vaporized liquid is water vapor, and wherein said gas atmosphere is ambient atmosphere.

10. Apparatus for detecting icing conditions on a monitored surface, comprising first means for creating a first output signal indicating that said surface has attained a temperature equivalent to a predetermined temperature, second means for creating a second output signal indicating the atmospheric dew point temperature, third means for creating a third output signal indicating the ambient atmospheric temperature, and summing means for receiving as input signals thereto said first second and third output signals to cause actuation of related output means, said summing means being ineffective to cause actuation of said related output means when said second and third output signals are received by said summing means but said first output signal is not received by said summing means.

11. In an atmospheric condition detecting and indicating apparatus having first means for producing a first output signal indicative of a selected freezing reference temperature, second means for producing a second output signal indicative of the dew point temperature of said atmosphere, and output means effective to be acted upon by said first and second output signals as to cause said output means to respond thereto, the improvement of having said second means comprise photo-optic hygrometer means, said photo-optic hygrometer means comprising thermocooler means having light reflecting surface means, an infrared light emitting diode, a phototransistor, said diode being effective to direct a beam of infrared light against said surface means as to cause said light to be reflected from said surface means and onto said phototransistor, said reflected light being of sufficient energy to place said phototransistor into conduction when said surface means is devoid of any atmospheric formation thereon, said phototransistor being effective when in conduction to energize related P-N junction device means in order to thereby cool said surface means to a temperature at which an atmospheric formation becomes present on said surface means, said reflected light being of insufficient energy to place said phototransistor into conduction when said atmospheric formation becomes present on said surface means, said phototransistor being effective when not in conduction to permit said surface means to become slightly heated to thereby remove said atmospheric formation from said surface means and to again cyclicly enable said reflected light to cause said phototransistor to go into conduction and thereby determine the magnitude of said dew point temperature as being generally in a range of temperatures with such range having as one limit the magnitude of the temperature of said surface means necessary to evaporate therefrom said atmospheric formation and having as the other limit the magnitude of the temperature of said surface means at which said atmospheric formation becomes present on said surface means.

12. Apparatus according to claim 11 wherein said light emitting diode is cyclically pulsed into energization as to thereby cause said beam of infrared light to also be cyclically emitted therefrom.

13. Apparatus according to claim 11 and further comprising additional means for sensing actual atmospheric temperature and creating a temperature signal in response thereto, means for comparing said dew point temperature and said temperature signal and effective for producing an output whenever the compared relationship of said dew point temperature and said temperature signal attains a predetermined relationship.

14. In an atmospheric condition detecting and indicating apparatus having first means for producing a first output signal indicative of a selected freezing reference temperature, second means for producing a second output signal indicative of the dew point temperature of said atmosphere and output means effective to be acted upon by said first and second output signals as to cause said output means to respond thereto, the improvement of having said second means comprise a photo-optic hygrometer means, said photo-optic hygrometer means comprising thermocooler means having light reflecting surface means, an infrared light emitting diode, a photo-transistor, said diode being effective to direct a beam of infrared light against said surface means as to cause said light to be reflected from said surface means and onto said photo-transistor, said reflected light being of sufficient energy to place said phototransistor into conduction when said surface means is devoid of any atmospheric formation thereon, said phototransistor being effective when in conduction to energize related P-N junction device means in order to thereby cool said surface means to a temperature at which an atmospheric formation becomes present on said surface means, said reflected light being of insufficient energy to place said phototransistor into conduction when said atmospheric formation becomes present on said surface means, said phototransistor being effective when not in conduction to permit said surface means to become slightly heated to thereby remove said atmospheric formation from said surface means and to again cyclically enable said reflected light to ccause said phototransistor to go into conduction and thereby determine the magnitude of said dew point temperature as being generally in a range of temperatures with such range having as one limit the magnitude of the temperature of said surface means necessary to evaporate therefrom said atmospheric formation and having as the other limit the magnitude of the temperature of said surface means at which said atmospheric formation becomes present on said surface means, and further comprising a second infrared light emitting diode, a second phototransistor, a second surface means the temperature of which is ambiently determined, said second diode being effective to direct a second beam of infrared light against said second surface means as to cause said second beam of light to be reflected onto said second phototransistor to thereby place said second phototransistor into conduction, said second phototransistor being in parallel with said first mentioned phototransistor as to thereby serve as a variable reference to thereby compensate for possible tendencies to operationally drift because of influencing adverse temperatures.

15. Atmospheric condition detecting and indicating apparatus, comprising first means for establishing and producing a first signal indicative of a first reference temperature, second means for sensing ambient atmospheric temperature and effective for producing a second signal indicative of the magnitude of said sensed ambient atmospheric temperature, and third means for receiving and comparing said first and second signals in order to determine whether said ambient temperature is of a magnitude greater than the magnitude of said reference temperature, said third means being effective for producing a resulting output signal only when the magnitude of said ambient temperature is equal to or less than the magnitude of said reference temperature.

16. Apparatus according to claim 15 wherein said first temperature is the dew point temperature, and further comprising fourth means effective for sensing and producing a fourth signal indicative of a monitored surface temperature, and fifth means for receiving said output signal and said fourth signal and in turn producing a second output signal in accordance with said output signal and said fourth signal.

17. A method of determining the dew point temperature of a vaporized liquid carried within a gas atmosphere comprising the steps of placing a gauging surface in intimate contact with said gas atmosphere, directing a beam of infrared light from a light source and against such gauging surface as to reflect said beam of light at an angle therefrom and against photosensitive means thereby causing said photosensitive means to be conductive and to energize associated means to cool said gauging surface, thusly cooling said gauging surface, until the vaporized liquid starts to precipitate from suspension as a dew onto said gauging surface, continuing to reflect said beam of light at said angle and employing said dew to absorb a sufficient degree of said infrared light beam as to thereby reduce the level of infrared energy reflected at said angle to said photosensitive means to thereby cause said photosensitive means to become non-conductive and thereby terminate further cooling of said gauging surface and to simultaneously initiate heating of said gauging surface, continuing to heat said gauging surface to evaporate said dew as to thereby terminate said absorption of said infrared light and to again permit said infrared light to be reflected from said gauging surface to said photosensitive means at an energy level sufficient to again repeat the cooling portion of the operating cycle, and monitoring the temperature of said gauging surface to determine the temperature at which such infrared light energy was sufficiently absorbed and employing such determined temperature as an indication of said dew point temperature.

18. The method according to claim 17 wherein the step of directing a beam of infrared light against said gauging surface comprises the step of cyclically energizing and de-energizing said light source as to thereby cause pulsing said beam of infrared light.

19. The method according to claim 17 and further comprising the step of monitoring the temperature of said gauging surface to determine the temperature at which said dew was evaporated and employing such temperature along with the temperature at which such infrared light energy was sufficiently absorbed as an indication of said dew point temperature.

20. The method according to claim 19 and further comprising the step of employing the temperature at which said dew was evaporated and the temperature at which such infrared light energy was sufficiently absorbed to define therebetween a very narrow range of temperatures which range contains the exact theoretical dew point temperature.

21. The method according to claim 17 and further comprising the steps of comparing said dew point temperature to the temperature of said gas atmosphere, and producing an output signal to associated output signal receiving means when the compared relationship of said dew point temperature and the temperature of said gas atmosphere attains a predetermined relationship.

22. Apparatus for detecting the presence of monitored substance on a gauging surface, comprising an infrared light generating source for directing a beam of infrared light against said gauging surface as to cause said beam of infrared light to be reflected therefrom, and an infrared light sensitive member having an actuating energy threshold positioned as to be acted upon by said reflected beam of infrared light to thereby create an output indicative thereof, said reflected beam of infrared light being the sole source for conveying light energy to said light sensitive member, said infrared light beam having a spectral range and energy level and said monitored substance having absorption characteristics as to cause absorption of a significant portion of the energy of said beam of infrared light by said monitored substance when said monitored substance is present on said gauging surface to thereby reduce the energy of said beam of infrared light impinging on said light sensitive means to a valve below said energy threshold and thereby alter the action of said light sensitive means in accordance with said absorption.

* * * * *